United States Patent [19]
Radford et al.

[11] Patent Number: 5,834,191
[45] Date of Patent: Nov. 10, 1998

[54] PRODUCTION OF HETEROLOGOUS PEPTIDES

[75] Inventors: Alan Radford, Homforth; John Howard Parish, Harrogate, both of United Kingdom

[73] Assignee: Neugenesis Corporation, Honolulu, Hi.

[21] Appl. No.: 596,300

[22] PCT Filed: Aug. 15, 1994

[86] PCT No.: PCT/GB94/01789
    § 371 Date: Feb. 13, 1996
    § 102(e) Date: Feb. 13, 1996

[87] PCT Pub. No.: WO95/05474
    PCT Pub. Date: Feb. 23, 1995

[30]     Foreign Application Priority Data

Aug. 13, 1993 [GB] United Kingdom ............ 9316883

[51] Int. Cl.[6] ............... C12Q 1/68; C12N 9/34; C12N 15/81; C07H 21/04
[52] U.S. Cl. ........... 435/6; 435/69.1; 435/91.4; 435/205; 435/254.4; 435/320.1; 536/23.1; 536/24.33
[58] Field of Search ............ 435/6, 69.1, 91.4, 435/205, 254.4, 320.1; 536/23.1, 24.1, 24.33

[56]      References Cited

U.S. PATENT DOCUMENTS 5,252,726  10/1993  Woldike ................. 536/24.1

FOREIGN PATENT DOCUMENTS 0225078    6/1987   European Pat. Off. .
WO 86/06097  10/1986  WIPO .
WO 89/01969   3/1989  WIPO .

OTHER PUBLICATIONS

Koh–Luar et al. (1989) Enz. Microb. Technol. 11:692–5.
Stone et al. (1993) Curr. Genet. 24:205–11.

*Primary Examiner*—David Guzo
*Assistant Examiner*—William Sandals
*Attorney, Agent, or Firm*—Klauber & Jackson

[57]      ABSTRACT

The invention relates to a method and recombinant means for engineering the production of heterologous peptides in filamentous fungus. The invention involves the genetic manipulation of the glucoamylase gene in order to provide a restriction site in same so that the promoter sequence of the glucoamylase gene can be coupled to a sequence encoding a heterologous peptide whereby the production of the peptide will be under the control of the promoter sequence of the glucoamylase gene.

26 Claims, 24 Drawing Sheets

FIGURE 1 A

```
ATCGATGGCA GCCACCATTC ATTTCTCGAT GCGACGGTAA ACGACGCCCG CGGCAGATTA      60

GGTCATTGCC GAACGGATTG AAGCTCTCTC CATCTTGGAT CCATTCCCGG CCAATCCCGT     120

CTCGGCCAAC CACACTGTCC ACTCGCCCAG GTCAGCAGCT CAGGACTCTC TCCTGGTTTG     180

GTACCGCTTA GTGTAGAGCA TACCGCTCTC AGTCCCCATA GACCAACCAT AACACCGCAC     240

GTTCTCTTTC ACTCAAGATG CTTATCATGT CCCCTCTTTC TGCTCCAATG ATTCGGACTG     300

GTCGAATACC AATGAGACAA GCGAGAGCGC AGTGCGAGCA AGCGTTCCTG CAGATAGAGC     360

AGTGGGACTG CCGCGCCACA AAGGAAGAGG ATCGTGACGT GACGTGACCA GTGACCAGAA     420

AGCAGAAGAT CCAAAAGAGT CAAAAGGACC GAGCCTCACC TACAGTAATG GCCCGGATGG     480

CACTCAAGAC CGTCCTCTCG GCCCTTTCTC CAACTCTTCT CCTTCCATAA TTCACCTAGG     540

TACATACACG GCCTACGCTT CCGCCTCATC CCATCCCATC CCATCCCATC CCATCCCATC     600

GACGACTCTA ACCCGCCCGC GAGTGCAAAC CTCGTCCACG AACGGACACC CCGGCTCTCC     660

TCCGAAGCCC TTGCAAGTGG AAGCTGAGGT TGCCGAACTT AGACGACCAG GTTCACCAGC     720

CGGACCGCAA CTCGAACGTC AGAATACAGC CTCAGCCTCC AAAGGGGGTT AACGCCAAGC     780

GAGAGCAAGA CAAGATCGTC GCCCATCAAT ATCCTGGACA AGACAACATG GACGCAATAT     840

ATAACCTCAA GCAAGTCCTC CTCAGCAACC ATGATTTCAC CACCAGCCTG GTCTCCAACG     900

CAACAGACTT CTCGACAAGT CCCTTGACCT ACTTCGCC ATG CAT CTC GTC TCT         953
                                           Met His Leu Val Ser
                                             1               5

TCG CTC CTC GTC GTG GGC GCC GCC TTC CAG GCC GTG CTC GGT CTG CCG      1001
Ser Leu Leu Val Val Gly Ala Ala Phe Gln Ala Val Leu Gly Leu Pro
            10                  15                  20

GAT CCT CTG CAT GAA AAG AGG CAC AGC GAC ATC ATC AAG CGG TCT GTC      1049
Asp Pro Leu His Glu Lys Arg His Ser Asp Ile Ile Lys Arg Ser Val
            25                  30                  35

GAC TCG TAT ATC CAG ACC GAG ACT CCC ATT GCG CAG AAG AAC CTT CTG      1097
Asp Ser Tyr Ile Gln Thr Glu Thr Pro Ile Ala Gln Lys Asn Leu Leu
            40                  45                  50

TGC AAC ATC GGT GCT TCT GGA TGC AGA GCC TCC GGT GCT GCC TCT GGT      1145
Cys Asn Ile Gly Ala Ser Gly Cys Arg Ala Ser Gly Ala Ala Ser Gly
            55                  60                  65

GTT GTG GTT GCC TCC CCT TCC AAG TCG AGC CCT GAC TGTAAGTG             1189
Val Val Val Ala Ser Pro Ser Lys Ser Ser Pro Asp
            70                  75              80

GAAATTGCAC AGTGTGTCTC ATCTCTCATG GCAGCATAGC TCACAGTGTC GATAGAC       1246
```

FIGURE 1 B

```
TGG TAT ACC TGG ACT CGT GAT GCC GCC CTT GTC ACC AAG CTT ATT GTC     1294
Trp Tyr Thr Trp Thr Arg Asp Ala Ala Leu Val Thr Lys Leu Ile Val
 1           5                   10                  15

GAC GAA TTC ACC AAC GAC TAC AAC ACC ACT CTT CAG AAC ACC ATT CAG     1342
Asp Glu Phe Thr Asn Asp Tyr Asn Thr Thr Leu Gln Asn Thr Ile Gln
             20                  25                  30

GCT TAT GCT GCT GCA CAG GCC AAG CTT CAG GGC GTT AGC AAC CCG TCC     1390
Ala Tyr Ala Ala Ala Gln Ala Lys Leu Gln Gly Val Ser Asn Pro Ser
         35                  40                  45

GGT TCC CTC TCC AAC GGG GCC GGT CTT GGT GAG CCC AAG TTC ATG GTC     1438
Gly Ser Leu Ser Asn Gly Ala Gly Leu Gly Glu Pro Lys Phe Met Val
 50                  55                  60

GAC CTC CAG CAG TTC ACC GGT GCC TGG GGC CGC CCC CAG AGG GAT GGC     1486
Asp Leu Gln Gln Phe Thr Gly Ala Trp Gly Arg Pro Gln Arg Asp Gly
 65                  70                  75                  80

CCT CCC CTT CGC GCC ATT GCC CTG ATC GGC TAT GGC AAG TGG CTC GTC     1534
Pro Pro Leu Arg Ala Ile Ala Leu Ile Gly Tyr Gly Lys Trp Leu Val
             85                  90                  95

AGC AAC GGT TAT GCT GAT ACG GCC AAG AGC ATC ATC TGG CCC ATT GTG     1582
Ser Asn Gly Tyr Ala Asp Thr Ala Lys Ser Ile Ile Trp Pro Ile Val
         100                 105                 110

AAG AAC GAC CTT GCC TAC ACT GCC CAG TAC TGG AAC AAC ACT GGC TTC     1630
Lys Asn Asp Leu Ala Tyr Thr Ala Gln Tyr Trp Asn Asn Thr Gly Phe
         115                 120                 125

GAT CTC TGG GAG GAG GTT AAC AGC TCT TCT TTC TTC ACC ATC GCC GCC     1678
Asp Leu Trp Glu Glu Val Asn Ser Ser Ser Phe Phe Thr Ile Ala Ala
 130                 135                 140

TCC CAC CGT GCT CTC GTT GAG GGT TCT GCT TTT GCC AAG TCC GTC GGC     1726
Ser His Arg Ala Leu Val Glu Gly Ser Ala Phe Ala Lys Ser Val Gly
145                  150                 155                 160

AGC TCT TGC AGC GCT TGC GAT GCC ATT GCC CCC CAA ATT CTG TGC TTC     1774
Ser Ser Cys Ser Ala Cys Asp Ala Ile Ala Pro Gln Ile Leu Cys Phe
             165                 170                 175

CAG CAG AGC TTC TGG TCC AAC AGC GGC TAC ATC ATC TCC AAC TTT GTC     1822
Gln Gln Ser Phe Trp Ser Asn Ser Gly Tyr Ile Ile Ser Asn Phe Val
         180                 185                 190

AAC TAC CGC AGC GGC AAG GAC ATC AAC TCC GTC TTG ACT TCC ATC CAC     1870
Asn Tyr Arg Ser Gly Lys Asp Ile Asn Ser Val Leu Thr Ser Ile His
         195                 200                 205

AAC TTC GAC CCC GCT GCC GGT TGC GAT GTC AAC ACC TTC CAG CCC TGC     1918
Asn Phe Asp Pro Ala Ala Gly Cys Asp Val Asn Thr Phe Gln Pro Cys
 210                 215                 220
```

FIGURE 1 C

```
AGC GAC CGG GCT CTT GCC AAC CAC AAG GTT GTC GTT GAC TCC ATG CGC        1966
Ser Asp Arg Ala Leu Ala Asn His Lys Val Val Val Asp Ser Met Arg
225                 230                 235                 240

TTC TGG GGT GTC AAC TCC GGT CGC ACT GCC GGT AAG GCC GCC GCT GTC        2014
Phe Trp Gly Val Asn Ser Gly Arg Thr Ala Gly Lys Ala Ala Ala Val
                245                 250                 255

GGT CGC TAC GCT GAG GAT GTC TAC TAC AAC GGT AAC CCG TGG TAC CTC        2062
Gly Arg Tyr Ala Glu Asp Val Tyr Tyr Asn Gly Asn Pro Trp Tyr Leu
            260                 265                 270

GCT ACT CTC GCC GCC GCC GAG CAG CTC TAC GAC GCC GTC TAC GTC TGG        2110
Ala Thr Leu Ala Ala Ala Glu Gln Leu Tyr Asp Ala Val Tyr Val Trp
        275                 280                 285

AAG AAG CAG GGT TCT ATC ACT GTC ACC TCC ACC TCC CTC GCC TTC TTC        2158
Lys Lys Gln Gly Ser Ile Thr Val Thr Ser Thr Ser Leu Ala Phe Phe
290                 295                 300

AAG GAC CTC GTT CCC TCC GTC AGC ACC GGC ACC TAC TCC AGC TCT TCC        2206
Lys Asp Leu Val Pro Ser Val Ser Thr Gly Thr Tyr Ser Ser Ser Ser
305                 310                 315                 320

TCC ACC TAC ACC GCC ATC ATC AAC GCC GTC ACC ACC TAT GCC GAC GGC        2254
Ser Thr Tyr Thr Ala Ile Ile Asn Ala Val Thr Thr Tyr Ala Asp Gly
                325                 330                 335

TTC GTC GAC ATC GTT GCC CAG TAC ACT CCC TCC GAC GGC TCC CTG GCC        2302
Phe Val Asp Ile Val Ala Gln Tyr Thr Pro Ser Asp Gly Ser Leu Ala
            340                 345                 350

GAG CAG TTC GAC AAG GAT TCG GGC GCC CCC CTC AGC GCC ACC CAC CTG        2350
Glu Gln Phe Asp Lys Asp Ser Gly Ala Pro Leu Ser Ala Thr His Leu
        355                 360                 365

ACC TGG TCG TAC GCC TCC TTC CTT TCC GCC GCC GCC CGC CGC GCC GGC        2398
Thr Trp Ser Tyr Ala Ser Phe Leu Ser Ala Ala Ala Arg Arg Ala Gly
370                 375                 380

ATC GTC CCT CCC TCG TGG GGC GCC GCG TCC GCC AAC TCT CTG CCC GGT        2446
Ile Val Pro Pro Ser Trp Gly Ala Ala Ser Ala Asn Ser Leu Pro Gly
385                 390                 395                 400

TCC TGC TCC GCC TCC ACC GTC GCC GGT TCA TAC GCC ACC GCG ACT GCC        2494
Ser Cys Ser Ala Ser Thr Val Ala Gly Ser Tyr Ala Thr Ala Thr Ala
                405                 410                 415

ACC TCC TTT CCC GCC AAC CTC ACG CCC GCC AGC ACC ACC GTC ACC CCT        2542
Thr Ser Phe Pro Ala Asn Leu Thr Pro Ala Ser Thr Thr Val Thr Pro
            420                 425                 430

CCC ACG CAG ACC GGC TGC GCC GCC GAC CAC GAG GTT TTG GTA ACT TTC        2590
Pro Thr Gln Thr Gly Cys Ala Ala Asp His Glu Val Leu Val Thr Phe
        435                 440                 445
```

FIGURE 1 D

```
AAC GAA AAG GTC ACC ACC AGC TAT GGT CAG ACG GTC AAG GTC GTC GGC        2638
Asn Glu Lys Val Thr Thr Ser Tyr Gly Gln Thr Val Lys Val Val Gly
    450                 455                 460

AGC ATC GCT CGG CTC GGC AAC TGG GCC CCC GCC AGC GGG CTC ACC CTG        2686
Ser Ile Ala Arg Leu Gly Asn Trp Ala Pro Ala Ser Gly Leu Thr Leu
465                 470                 475                 480

TCG GCC AAA CAG TAC TCT TCC AGC AAC CCG CTC TGG TCC ACC ACT ATT        2734
Ser Ala Lys Gln Tyr Ser Ser Ser Asn Pro Leu Trp Ser Thr Thr Ile
                485                 490                 495

GCG CTG CCC CAG GGC ACC TCG TTC AAG TAC AAG TAT GTC GTC GTC AAC        2782
Ala Leu Pro Gln Gly Thr Ser Phe Lys Tyr Lys Tyr Val Val Val Asn
            500                 505                 510

TCG GAT GGG TCC GTC AAG TGG GAG AAC GAT CCT GAC CGC AGC TAT GCT        2830
Ser Asp Gly Ser Val Lys Trp Glu Asn Asp Pro Asp Arg Ser Tyr Ala
        515                 520                 525

GTT GGG ACG GAC TGC GCC TCT ACT GCG ACT CTT GAT GAT ACG TGG AGG        2876
Val Gly Thr Asp Cys Ala Ser Thr Ala Thr Leu Asp Asp Thr Trp Arg
    530                 535                 540

TAAATCGC TTGCTTCGTA CTAGGTAGTA AGTAGTGATT GGGAAAAGGA AATGAGAGAA        2936
***
CGGGAACGGG AACGGGAACG GGAATTTGTG ATTACAAAGT GTAAAATTAA TAGGCCCGGG     2996

ATTTTGGTTA GATGCATAAG GGGGGCAGGG GGGGCTAGGA AACGGAAGGT TGCATATCAA     3056

CCGAGGAAGA ATGGGAAGAA AGGGAAGAAA GACAGAAAGA AGGAACAACA GGACTTCATT     3116

CTCTCACATC GACATGAGCT ACCTGGGCAT CAGCTACCTG GCATCTTGA TTTCCTTTTT      3176

AGAAGATTGT TTTGTATCCT TTTTTCTTCC TCCCTTTTCT TTTCTTGTCC GTCTCTTACA     3236

CCTACCTATT TTTAGCCAAA GTCCACACAC ACACAAACTT TTTGTTAGAT ATTCTCTGTA     3296

TCAAAATTGA CAAGTTTCAA TGTTATACAG TACCTTGCCA AGTTTAATAC ACATTCAAAT     3356

CAATCAACCA CACACACACA AGTTTTATTG TGCAGAAATG GAGTGAAGAA GAAACATGTT     3416

TGGGATTATG ATGACAAGCT TCTCAACAAA ATTTCAACGA GTTAAGCTTC AAAGGTCCGC     3476

TGGCTCAATG GCAGAGCGTC TGACTACGAA TCAGGAGGTT CCAGGTTCGA CCCCTGGGTG     3536

GATCGAGTTG CAAATTGGTA CTTTGAGTAC CAAAGTTCCT TTTTTTTTTT CGTTTGGCTC     3596

TCTGCTTTTC GACAGTTCAC TGAGTCATGT GCAAGACACC CCTGATCGGG TACGTACTGA     3656

ACTGCTTTTG GTGCAGTGCA ATGGTTCTCG AGTGCAAGGG ATGAAAGGAA GATATGTCTT     3716

```
AAAAGCTGGA ATTCGAGCTC CACCGCGGTG GCGGCCGCTC TAGAACTAGT GGATCCCCCG      60
GGCTGCAGGA ATTCGATATC AAGCTTATCG ATGGCAGCCA CCATTCATTT CTCGATGCGA     120
CGGTAAACGA CGCCCGCGGC AGATTAGGTC ATTGCCGAAC GGATTGAAGC TCTCTCCATC     180
TTGGATCCAT TCCCGGCCAA TCCCGTCTCG GCCAACCACA CTGTCCACTC GCCCAGGTCA     240
GCAGCTCAGG ACTCTCTCCT GGTTTGGTAC CGCTTAGTGT AGAGCATACC GCTCTCAGTC     300
CCCATAGACC AACCATAACA CCGCACGTTC TCTTTCACTC AAGATGCTTA TCATGTCCCC     360
TCTTTCTGCT CCAATGATTC GGACTGGTCG AATACCAATG AGACAAGCGA GAGCGCAGTG     420
CGAGCAAGCG TTCCTGCAGA TAGAGCAGTG GGACTGCCGC GCCACAAAGG AAGAGGATCG     480
TGACGTGACG TGACCAGTGA CCAGAAAGCA GAAGATCCAA AAGAGTCAAA AGGACCGAGC     540
CTCACCTACA GTAATGGCCC GGATGGCACT CAAGACCGTC CTCTCGGCCC TTTCTCCAAC     600
TCTTCTCCTT CCATAATTCA CCTAGGTACA TACACGGCCT ACGCTTCCGC CTCATCCCAT     660
CCCATCCCAT CCCATCCCAT CCCATCGACG ACTCTAACCC GCCCGCGAGT GCAAACCTCG     720
TCCACGAACG GACACCCCGG CTCTCCTCCG AAGCCCTTGC AAGTGGAAGC TGAGGTTGCC     780
GAACTTAGAC GACCAGGTTC ACCAGCCGGA CCGCAACTCG AACGTCAGAA TACAGCCTCA     840
GCCTCCAAAG GGGGTTAACG CCAAGCGAGA GCAAGACAAG ATCGTCGCCC ATCAATATCC     900
TGGACAAGAC AACATGGACG CAATATATAA CCTCAAGCAA GTCCTCCTCA GCAACCATGA     960
TTTCACCACC AGCCTGGTCT CCAACGCAAC AGACTTCTCG ACAAGTCCCT TGACCTACTT    1020
CGCCATGCAT CTCGTCTCTT CGCTCCTCGT CGTGGGCGCC GCCTTCCAGG CCGTGCTCGG    1080
TCTGCCGGAT CCTCTGCATG AAAAGAGGCA CAGCGACATC ATCAAGCGGT CTGTCGACTC    1140
GTATATCCAG ACCGAGACTC CCATTGCGCA GAAGAACCTT CTGTGCAACA TCGGTGCTTC    1200
TGGATGCAGA GCCTCCGGTG CTGCCTCTGG TGTTGTGGTT GCCTCCCCTT CCAAGTCGAG    1260
CCCTGACTGT AAGTGGAAAT TGCACAGTGT GTCTCATCTC TCATGGCAGC ATAGCTCACA    1320
GTGTCGATAG ACTGGTATAC CTGGACTCGT GATGCCGCCC TTGTCACCAA GCTTATTGTC    1380
GACGAATTCA CCAACGACTA CAACACCACT CTTCAGAACA CCATTCAGGC TTATGCTGCT    1440
GCACAGGCCA AGCTTCAGGG CGTTAGCAAC CCGTCCGGTT CCCTCTCCAA CGGGGCCGGT    1500
CTTGGTGAGC CCAAGTTCAT GGTCGACCTC CAGCAGTTCA CCGGTGCCTG GGGCCGCCCC    1560
CAGAGGGATG GCCCTCCCCT TCGCGCCATT GCCCTGATCG CTATGGCAA GTGGCTCGTC     1620
```

FIGURE 3 B

```
AGCAACGGTT ATGCTGATAC GGCCAAGAGC ATCATCTGGC CCATTGTGAA GAACGACCTT   1680

GCCTACACTG CCCAGTACTG GAACAACACT GGCTTCGATC TCTGGGAGGA GGTTAACAGC   1740

TCTTCTTTCT TCACCATCGC CGCCTCCCAC CGTGCTCTCG TTGAGGGTTC TGCTTTTGCC   1800

AAGTCCGTCG GCAGCTCTTG CAGCGCTTGC GATGCCATTG CCCCCCAAAT TCTGTGCTTC   1860

CAGCAGAGCT TCTGGTCCAA CAGCGGCTAC ATCATCTCCA ACTTTGTCAA CTACCGCAGC   1920

GGCAAGGACA TCAACTCCGT CTTGACTTCC ATCCACAACT TCGACCCCGC TGCCGGTTGC   1980

GATGTCAACA CCTTCCAGCC CTGCAGCGAC CGGGCTCTTG CCAACCACAA GGTTGTCGTT   2040

GACTCCATGC GCTTCTGGGG TGTCAACTCC GGTCGCACTG CCGGTAAGGC CGCCGCTGTC   2100

GGTCGCTACG CTGAGGATGT CTACTACAAC GGTAACCCGT GGTACCTCGC TACTCTCGCC   2160

GCCGCCGAGC AGCTCTACGA CGCCGTCTAC GTCTGGAAGA AGCAGGGTTC TATCACTGTC   2220

ACCTCCACCT CCCTCGCCTT CTTCAAGGAC CTCGTTCCCT CCGTCAGCAC CGGCACCTAC   2280

TCCAGCTCTT CCTCCACCTA CACCGCCATC ATCAACGCCG TCACCACCTA TGCCGACGGC   2340

TTCGTCGACA TCGTTGCCCA GTACACTCCC TCCGACGGCT CCCTGGCCGA GCAGTTCGAC   2400

AAGGATTCGG GCGCCCCCCT CAGCGCCACC CACCTGACCT GGTCGTACGC CTCCTTCCTT   2460

TCCGCCGCCG CCCGCCGCGC CGGCATCGTC CCTCCCTCGT GGGGCGCCGC GTCCGCCAAC   2520

TCTCTGCCCG GTTCCTGCTC CGCCTCCACC GTCGCCGGTT CATACGCCAC CGCGACTGCC   2580

ACCTCCTTTC CGCCAACCT CACGCCCGCC AGCACCACCG TCACCCCTCC CACGCAGACC   2640

GGCTGCGCCG CCGACCACGA GGTTTTGGTA ACTTTCAACG AAAAGGTCAC CACCAGCTAT   2700

GGTCAGACGG TCAAGGTCGT CGGCAGCATC GCTCGGCTCG GCAACTGGGC CCCCGCCAGC   2760

GGGCTCACCC TGTCGGCCAA ACAGTACTCT TCCAGCAACC CGCTCTGGTC CACCACTATT   2820

GCGCTGCCCC AGGGCACCTC GTTCAAGTAC AAGTATGTCG TCGTCAACTC GGATGGGTCC   2880

GTCAAGTGGG AGAACGATCC TGACCGCAGC TATGCTGTTG GGACGGACTG CGCCTCTACT   2940

GCGACTCTTG ATGATACGTG GAGGTAAATC GCTTGCTTCG TACTAGGTAG TAAGTAGTGA   3000

TTGGGAAAAG GAAATGAGAG AACGGGAACG GGAACGGGAA CGGGAATTTG TGATTACAAA   3060

GTGTAAAATT AATAGGCCCG GGATTTTGGT TAGATGCATA AGGGGGGCAG GGGGGGCTAG   3120

GAAACGGAAG GTTGCATATC AACCGAGGAA GAATGGGAAG AAAGGGAAGA AAGACAGAAA   3180

GAAGGAACAA CAGGACTTCA TTCTCTCACA TCGACATGAG CTACCTGGGC ATCAGCTACC   3240
```

FIGURE 3 C

```
TGGGCATCTT GATTTCCTTT TTAGAAGATT GTTTTGTATC CTTTTTTCTT CCTCCCTTTT    3300

CTTTTCTTGT CCGTCTCTTA CACCTACCTA TTTTTAGCCA AAGTCCACAC ACACACAAAC    3360

TTTTTGTTAG ATATTCTCTG TATCAAAATT GACAAGTTTC AATGTTATAC AGTACCTTGC    3420

CAAGTTTAAT ACACATTCAA ATCAATCAAC CACACACACA CAAGTTTTAT TGTGCAGAAA    3480

TGGAGTGAAG AAGAAACATG TTTGGGATTA TGATGACAAG CTTCTCAACA AAATTTCAAC    3540

GAGTTAAGCT TCAAAGGTCC GCTGGCTCAA TGGCAGAGCG TCTGACTACG AATCAGGAGG    3600

TTCCAGGTTC GACCCCTGGG TGGATCGAGT TGCAAATTGG TACTTTGAGT ACCAAAGTTC    3660

CTTTTTTTTT TTCGTTTGGC TCTCTGCTTT TCGACAGTTC ACTGAGTCAT GTGCAAGACA    3720

CCCCTGATCG GGTACGTACT GAACTGCTTT TGGTGCAGTG CAATGGTTCT CGAGGGGGGG    3780

CCCGGTACCC AATTCG                                                    3796
```

FIG.4

```
5' primer at the Ppum I site :
CCTTCTTCAAGGACCTCGTTCCCTCCG
5'                         3'

5'        Ppum I        3'
             CCTTCTTCAAGGACCTCGTTCCCTCCG
             | | | | | | | | | | | | | | | | | | | | | | | | | | |
gla I :CCACCTCCCTCGCCTTCTTCAAGGACCTCGTTCCCTCCGTCAGCAC
                      |                         |
                    2163                      2189
```

---

```
3' primer containing the Mro I site :
GGCGATTTACCTCCGGATATCATCAAGAGTCG
3'                              5'

2867                           2899
           |                              |
gla I : TACTGCGACTCTTGATGATACGTGGAGGTAAATCGCTTgcttcgtacta
        | | | | | | | | | | | | XXX | | | | | | | | | |
        GCGACTCTTGATGATATCCGGAGGTAAATCGC
         3'              Mro I          5'
```

FIGURE 5 A

```
AAAAGCTGGA ATTCGAGCTC CACCGCGGTG GCGGCCGCTC TAGAACTAGT GGATCCCCG      60
GGCTGCAGGA ATTCGATATC AAGCTTATCG ATGGCAGCCA CCATTCATTT CTCGATGCGA    120
CGGTAAACGA CGCCCGCGGC AGATTAGGTC ATTGCCGAAC GGATTGAAGC TCTCTCCATC    180
TTGGATCCAT TCCCGGCCAA TCCCGTCTCG GCCAACCACA CTGTCCACTC GCCCAGGTCA    240
GCAGCTCAGG ACTCTCTCCT GGTTTGGTAC CGCTTAGTGT AGAGCATACC GCTCTCAGTC    300
CCCATAGACC AACCATAACA CCGCACGTTC TCTTTCACTC AAGATGCTTA TCATGTCCCC    360
TCTTTCTGCT CCAATGATTC GGACTGGTCG AATACCAATG AGACAAGCGA GAGCGCAGTG    420
CGAGCAAGCG TTCCTGCAGA TAGAGCAGTG GGACTGCCGC GCCACAAAGG AAGAGGATCG    480
TGACGTGACG TGACCAGTGA CCAGAAAGCA GAAGATCCAA AAGAGTCAAA AGGACCGAGC    540
CTCACCTACA GTAATGGCCC GGATGGCACT CAAGACCGTC CTCTCGGCCC TTTCTCCAAC    600
TCTTCTCCTT CCATAATTCA CCTAGGTACA TACACGGCCT ACGCTTCCGC CTCATCCCAT    660
CCCATCCCAT CCCATCCCAT CCCATCGACG ACTCTAACCC GCCGCGAGT GCAAACCTCG     720
TCCACGAACG GACACCCCGG CTCTCCTCCG AAGCCCTTGC AAGTGGAAGC TGAGGTTGCC    780
GAACTTAGAC GACCAGGTTC ACCAGCCGGA CCGCAACTCG AACGTCAGAA TACAGCCTCA    840
GCCTCCAAAG GGGGTTAACG CCAAGCGAGA GCAAGACAAG ATCGTCGCCC ATCAATATCC    900
TGGACAAGAC AACATGGACG CAATATATAA CCTCAAGCAA GTCCTCCTCA GCAACCATGA    960
TTTCACCACC AGCCTGGTCT CCAACGCAAC AGACTTCTCG ACAAGTCCCT TGACCTACTT   1020
CGCCATGCAT CTCGTCTCTT CGCTCCTCGT CGTGGGCGCC GCCTTCCAGG CCGTGCTCGG   1080
TCTGCCGGAT CCTCTGCATG AAAAGAGGCA CAGCGACATC ATCAAGCGGT CTGTCGACTC   1140
GTATATCCAG ACCGAGACTC CCATTGCGCA GAAGAACCTT CTGTGCAACA TCGGTGCTTC   1200
TGGATGCAGA GCCTCCGGTG CTGCCTCTGG TGTTGTGGTT GCCTCCCCTT CCAAGTCGAG   1260
CCCTGACTGT AAGTGGAAAT TGCACAGTGT GTCTCATCTC TCATGGCAGC ATAGCTCACA   1320
GTGTCGATAG ACTGGTATAC CTGGACTCGT GATGCCGCCC TTGTCACCAA GCTTATTGTC   1380
GACGAATTCA CCAACGACTA CAACACCACT CTTCAGAACA CCATTCAGGC TTATGCTGCT   1440
GCACAGGCCA AGCTTCAGGG CGTTAGCAAC CCGTCCGGTT CCCTCTCCAA CGGGGCCGGT   1500
CTTGGTGAGC CCAAGTTCAT GGTCGACCTC CAGCAGTTCA CCGGTGCCTG GGGCCGCCCC   1560
```

FIGURE 5 B

```
CAGAGGGATG GCCCTCCCCT TCGCGCCATT GCCCTGATCG GCTATGGCAA GTGGCTCGTC    1620
AGCAACGGTT ATGCTGATAC GGCCAAGAGC ATCATCTGGC CCATTGTGAA GAACGACCTT    1680
GCCTACACTG CCCAGTACTG GAACAACACT GGCTTCGATC TCTGGGAGGA GGTTAACAGC    1740
TCTTCTTTCT TCACCATCGC CGCCTCCCAC CGTGCTCTCG TTGAGGGTTC TGCTTTTGCC    1800
AAGTCCGTCG GCAGCTCTTG CAGCGCTTGC GATGCCATTG CCCCCAAAT TCTGTGCTTC     1860
CAGCAGAGCT TCTGGTCCAA CAGCGGCTAC ATCATCTCCA ACTTTGTCAA CTACCGCAGC    1920
GGCAAGGACA TCAACTCCGT CTTGACTTCC ATCCACAACT TCGACCCCGC TGCCGGTTGC    1980
GATGTCAACA CCTTCCAGCC CTGCAGCGAC CGGGCTCTTG CCAACCACAA GGTTGTCGTT    2040
GACTCCATGC GCTTCTGGGG TGTCAACTCC GGTCGCACTG CCGGTAAGGC CGCCGCTGTC    2100
GGTCGCTACG CTGAGGATGT CTACTACAAC GGTAACCCGT GGTACCTCGC TACTCTCGCC    2160
GCCGCCGAGC AGCTCTACGA CGCCGTCTAC GTCTGGAAGA AGCAGGGTTC TATCACTGTC    2220
ACCTCCACCT CCCTCGCCTT CTTCAAGGAC CTCGTTCCCT CCGTCAGCAC CGGCACCTAC    2280
TCCAGCTCTT CCTCCACCTA CACCGCCATC ATCAACGCCG TCACCACCTA TGCCGACGGC    2340
TTCGTCGACA TCGTTGCCCA GTACACTCCC TCCGACGGCT CCCTGGCCGA GCAGTTCGAC    2400
AAGGATTCGG GCGCCCCCCT CAGCGCCACC CACCTGACCT GGTCGTACGC CTCCTTCCTT    2460
TCCGCCGCCG CCCGCCGCGC CGGCATCGTC CCTCCCTCGT GGGGCGCCGC GTCCGCCAAC    2520
TCTCTGCCCG GTTCCTGCTC CGCCTCCACC GTCGCCGGTT CATACGCCAC CGCGACTGCC    2580
ACCTCCTTTC CGCCAACCT CACGCCCGCC AGCACCACCG TCACCCCTCC CACGCAGACC     2640
GGCTGCGCCG CCGACCACGA GGTTTTGGTA ACTTTCAACG AAAAGGTCAC CACCAGCTAT    2700
GGTCAGACGG TCAAGGTCGT CGGCAGCATC GCTCGGCTCG GCAACTGGGC CCCCGCCAGC    2760
GGGCTCACCC TGTCGGCCAA ACAGTACTCT TCCAGCAACC CGCTCTGGTC CACCACTATT    2820
GCGCTGCCCC AGGGCACCTC GTTCAAGTAC AAGTATGTCG TCGTCAACTC GGATGGGTCC    2880
GTCAAGTGGG AGAACGATCC TGACCGCAGC TATGCTGTTG GGACGGACTG CGCCTCTACT    2940
GCGACTCTTG ATGATATCCG GAGGAGGTAA ATCGCCGGGG GCGCGCCGGA TCCTTAATTA    3000
AGTCTAGAGT CGACTGTTTA AACCTGCAGG CATGCAAGCT T                        3041
```

FIGURE 6 A

```
AAATTGTAAA CGTTAATATT TTGTTAAAAT TCGCGTTAAA TTTTTGTTAA ATCAGCTCAT    60
TTTTTAACCA ATAGGCCGAA ATCGGCAAAA TCCCTTATAA ATCAAAAGAA TAGACCGAGA   120
TAGGGTTGAG TGTTGTTCCA GTTTGGAACA AGAGTCCACT ATTAAAGAAC GTGGACTCCA   180
ACGTCAAAGG GCGAAAAACC GTCTATCAGG GCGATGGCCC ACTACGTGAA CCATCACCCT   240
AATCAAGTTT TTTGGGGTCG AGGTGCCGTA AAGCACTAAA TCGGAACCCT AAAGGGAGCC   300
CCCGATTTAG AGCTTGACGG GGAAAGCCGG CGAACGTGGC GAGAAAGGAA GGGAAGAAAG   360
CGAAAGGAGC GGGCGCTAGG GCGCTGGCAA GTGTAGCGGT CACGCTGCGC GTAACCACCA   420
CACCCGCCGC GCTTAATGCG CCGCTACAGG GCGCGTCCCA TTCGCCATTC AGGCTACGCA   480
ACTGTTGGGA AGGGCGATCG GTGCGGGCCT CTTCGCTATT ACGCCAGCTG GCGAAGGGG    540
GATGTGCTGC AAGGCGATTA AGTTGGGTAA CGCCAGGGTT TTCCCAGTCA CGACGTTGTA   600
AAACGACGGC CAGTGAATTG TAATACGACT CACTATAGGG CGAATTGAGC TCCACCGCGG   660
TGGCGGCCGC TCTAGCGATG GCAGCCACCA TTCATTTCTC GATGCGACGG TAAACGACGC   720
CCGCGGCAGA TTAGGTCATT GCCGAACGGA TTGAAGCTCT CTCCATCTTG GATCCATTCC   780
CGGCCAATCC CGTCTCGGCC AACCACACTG TCCACTCGCC CAGGTCAGCA GCTCAGGACT   840
CTCTCCTGGT TTGGTACCGC TTAGTGTAGA GCATACCGCT CTCAGTCCCC ATAGACCAAC   900
CATAACACCG CACGTTCTCT TTCACTCAAG ATGCTTATCA TGTCCCTCT TTCTGCTCCA    960
ATGATTCGGA CTGGTCGAAT ACCAATGAGA CAAGCGAGAG CGCAGTGCGA GCAAGCGTTC  1020
CTGCAGATAG AGCAGTGGGA CTGCCGCGCC ACAAAGGAAG AGGATCGTGA CGTGACGTGA  1080
CCAGTGACCA GAAAGCAGAA GATCCAAAAG AGTCAAAAGG ACCGAGCCTC ACCTACAGTA  1140
ATGGCCCGGA TGGCACTCAA GACCGTCCTC TCGGCCCTTT CTCCAACTCT TCTCCTTCCA  1200
TAATTCACCT AGGTACATAC ACGGCCTACG CTTCCGCCTC ATCCCATCCC ATCCCATCCC  1260
ATCCCATCCC ATCGACGACT CTAACCCGCC CGCGAGTGCA AACCTCGTCC ACGAACGGAC  1320
ACCCCGGCTC TCCTCCGAAG CCCTTGCAAG TGGAAGCTGA GGTTGCCGAA CTTAGACGAC  1380
CAGGTTCACC AGCCGGACCG CAACTCGAAC GTCAGAATAC AGCCTCAGCC TCCAAAGGGG  1440
GTTAACGCCA AGCGAGAGCA AGACAAGATC GTCGCCCATC AATATCCTGG ACAAGACAAC  1500
ATGGACGCAA TATATAACCT CAAGCAAGTC CTCCTCAGCA ACCATGATTT CACCACCAGC  1560
```

FIGURE 6 B

```
CTGGTCTCCA ACGCAACAGA CTTCTCGACA AGTCCCTTGA CCTACTTCGC CATGCATCTC    1620
GTCTCTTCGC TCCTCGTCGT GGGCGCCGCC TTCCAGGCCG TGCTCGGTCT GCCGGATCCT    1680
CTGCATGAAA AGAGGCACAG CGACATCATC AAGCGGTCTG TCGACTCGTA TATCCAGACC    1740
GAGACTCCCA TTGCGCAGAA GAACCTTCTG TGCAACATCG GTGCTTCTGG ATGCAGAGCC    1800
TCCGGTGCTG CCTCTGGTGT TGTGGTTGCC TCCCCTTCCA AGTCGAGCCC TGACTGTAAG    1860
TGGAAATTGC ACAGTGTGTC TCATCTCTCA TGGCAGCATA GCTCACAGTG TCGATAGACT    1920
GGTATACCTG GACTCGTGAT GCCGCCCTTG TCACCAAGCT TATTGTCGAC GAATTCCGGC    1980
GCGCCCCCGG GTTAATTAAG TCTAGAGTGG AGGTAAATCG CTTGCTTCGT ACTAGGTAGT    2040
AAGTAGTGAT TGGGAAAAGG AAATGAGAGA ACGGGAACGG GAACGGGAAC GGGAATTTGT    2100
GATTACAAAG TGTAAAATTA ATAGGCCCGG GATTTTGGTT AGATGCATAA GGGGGGCAGG    2160
GGGGGCTAGG AAACGGAAGG TTGCATATCA ACCGAGGAAG AATGGGAAGA AAGGGAAGAA    2220
AGACAGAAAG AAGGAACAAC AGGACTTCAT TCTCTCACAT CGACATGAGC TACCTGGGCA    2280
TCAGCTACCT GGGCATCTTG ATTTCCTTTT TAGAAGATTG TTTTGTATCC TTTTTTCTTC    2340
CTCCCTTTTC TTTTCTTGTC CGTCTCTTAC ACCTACCTAT TTTTAGCCAA AGTCCACACA    2400
CACACAAACT TTTTGTTAGA TATTCTCTGT ATCAAAATTG ACAAGTTTCA ATGTTATACA    2460
GTACCTTGCC AAGTTTAATA CACATTCAAA TCAATCAACC ACACACACAC AAGTTTTATT    2520
GTGCAGAAAT GGAGTGAAGA AGAAACATGT TTGGGATTAT GATGACAAGC TTCTCAACAA    2580
AATTTCAACG AGTTAAGCTT CAAAGGTCCG CTGGCTCAAT GGCAGAGCGT CTGACTACGA    2640
ATCAGGAGGT TCCAGGTTCG ACCCCTGGGT GGATCGAGTT GCAAATTGGT ACTTTGAGTA    2700
CCAAAGTTCC TTTTTTTTTT TCGTTTGGCT CTCTGCTTTT CGACAGTTCA CTGAGTCATG    2760
TGCAAGACAC CCCTGATCGG GTACGTACTG AACTGCTTTT GGTGCAGTGC AATGGTTCTC    2820
GAGGGGGGGC CCGGTACCCA GCTTTTGTTC CCTTTAGTGA GGGTTAATTC CGAGCTTGGC    2880
GTAATCATGG TCATAGCTGT TTCCTGTGTG AAATTGTTAT CCGCTCACAA TTCCACACAA    2940
CATAGGAGCC GGAAGCATAA AGTGTAAAGC CTGGGGTGCC TAATGAGTGA GGTAACTCAC    3000
ATTAATTGCG TTGCGCTCAC TGCCCGCTTT CCAGTCGGGA AACCTGTCGT GCCAGCTGCA    3060
TTAATGAATC GGCCAACGCG CGGGGAGAGG CGGTTTGCGT ATTGGGCGCT CTTCCGCTTC    3120
```

FIGURE 6C

```
CTCGCTCACT GACTCGCTGC GCTCGGTCGT TCGGCTGCGG CGAGCGGTAT CAGCTCACTC    3180
AAAGGCGGTA ATACGGTTAT CCACAGAATC AGGGGATAAC GCAGGAAAGA ACATGTGAGC    3240
AAAAGGCCAG CAAAAGGCCA GGAACCGTAA AAAGGCCGCG TTGCTGGCGT TTTTCCATAG    3300
GCTCGGCCCC CCTGACGAGC ATCACAAAAA TCGACGCTCA AGTCAGAGGT GGCGAAACCC    3360
GACAGGACTA TAAAGATACC AGGCGTTCCC CCCTGGAAGC TCCCTCGTGC GCTCTCCTGT    3420
TCCGACCCTG CCGCTTACCG GATACCTGTC CGCCTTTCTC CCTTCGGGAA GCGTGGCGCT    3480
TTCTCAATGC TCACGCTGTA GGTATCTCAG TTCGGTGTAG GTCGTTCGCT CCAAGCTGGG    3540
CTGTGTGCAC GAACCCCCCG TTCAGCCCGA CCGCTGCGCC TTATCCGGTA ACTATCGTCT    3600
TGAGTCCAAC CCGGTAAGAC ACGACTTATC GCCACTGGCA GCAGCCACTG GTAACAGGAT    3660
TAGCAGAGCG AGGTATGTAG GCGGTGCTAC AGAGTTCTTG AAGTGGTGGC CTAACTACGG    3720
CTACACTAGA AGGACAGTAT TTGGTATCTG CGCTCTGCTG AAGCCAGTTA CCTTCGGAAA    3780
AAGAGTTGGT AGCTCTTGAT CCGGCAAACA AACCACCGCT GGTAGCGGTG GTTTTTTTGT    3840
TTGCAAGCAG CAGATTACGC GCAGAAAAAA AGGATCTCAA GAAGATCCTT TGATCTTTTC    3900
TACGGGGTCT GACGCTCAGT GGAACGAAAA CTCACGTTAA GGGATTTTGG TCATGAGATT    3960
ATCAAAAGG ATCTTCACCT AGATCCTTTT AAATTAAAAA TGAAGTTTTA AATCAATCTA    4020
AAGTATATAT GAGTAAACTT GGTCTGACAG TTACCAATGC TTAATCAGTG AGGCACCTAT    4080
CTCAGCGATC TGTCTATTTC GTTCATCCAT AGTTGCCTGA CTGCCCGTCG TGTAGATAAC    4140
TACGATACGG GAGGGCTTAC CATCTGGCCC CAGTGCTGCA ATGATACCGC GAGACCCACG    4200
CTCACCGGCT CCAGATTTAT CAGCAATAAA CCAGCCAGCC GGAAGGGCCG AGCGCAGAAG    4260
TGGTCCTGCA ACTTTATCCG CCTCCATCCA GTCTATTAAT TGTTGCCGGG AAGCTAGAGT    4320
AAGTAGTTCG CCAGTTAATA GTTTGCGCAA CGTTGTTGCC ATTGCTACAG GCATCGTGGT    4380
GTCACGCTCG TCGTTTGGTA TGGCTTCATT CAGCTCCGGT TCCCAACGAT CAAGGCGAGT    4440
TACATGATCC CCCATGTTGT GAAAAAAAGC GGTTAGCTCC TTCGGTCCTC CGATCGTTGT    4500
CAGAAGTAAG TTGGCCGCAG TGTTATCACT CATGCTTATG GCAGCACTGC ATAATTCTCT    4560
TACTGTCATG CCATCCGTAA GATGCTTTTC TGTGACTGGT GAGTACTCAA CCAAGTCATT    4620
CTGAGAATAG TGTATGCGGC GACCGAGTTG CTCTTGCCCG GCGTCAATAC GGGATAATAC    4680
```

FIGURE 6 D

| | | | | | | |
|---|---|---|---|---|---|---|
| CGCGCCACAT | AGCAGAACTT | TAAAAGTGCT | CATCATTGGA | AAACGTTCTT | CGGGGCGAAA | 4740 |
| ACTCTCAAGG | ATCTTACCGC | TGTTGAGATC | CAGTTCGATG | TAACCCACTC | GTGCACCCAA | 4800 |
| CTGATCTTCA | GCATCTTTTA | CTTTCACCAG | CGTTTCTGGG | TGAGCAAAAA | CAGGAAGGCA | 4860 |
| AAATGCCGCA | AAAAAGGGAA | TAAGGGCGAC | ACGGAAATGT | TGAATACTCA | TACTCTTCCT | 4920 |
| TTTTCAATAT | TATTGAAGCA | TTTATCAGGG | TTATTGTCTC | ATGAGCGGAT | ACATATTTGA | 4980 |
| ATGTATTTAG | AAAAATAAAC | AAATAGGGGT | TCCGCGCACA | TTTCCCCGAA | AAGTGCCACC | 5040 |
| TG | | | | | | 5042 |

FIGURE 7 A

```
ATG CAT CTC GTC TCT TCG CTC CTC GTC GTG GGC GCC GCC TTC CAG GCC      48
Met His Leu Val Ser Ser Leu Leu Val Val Gly Ala Ala Phe Gln Ala
    545             550             555

GTG CTC GGT CTG CCG GAT CCT CTG CAT GAA AAG AGG CAC AGC GAC ATC      96
Val Leu Gly Leu Pro Asp Pro Leu His Glu Lys Arg His Ser Asp Ile
560             565             570             575

ATC AAG CGG TCT GTC GAC TCG TAT ATC CAG ACC GAG ACT CCC ATT GCG     144
Ile Lys Arg Ser Val Asp Ser Tyr Ile Gln Thr Glu Thr Pro Ile Ala
                580             585             590

CAG AAG AAC CTT CTG TGC AAC ATC GGT GCT TCT GGA TGC AGA GCC TCC     192
Gln Lys Asn Leu Leu Cys Asn Ile Gly Ala Ser Gly Cys Arg Ala Ser
            595             600             605

GGT GCT GCC TCT GGT GTT GTG GTT GCC TCC CCT TCC AAG TCG AGC CCT     240
Gly Ala Ala Ser Gly Val Val Val Ala Ser Pro Ser Lys Ser Ser Pro
        610             615             620

GAC TAC TGG TAT ACC TGG ACT CGT GAT GCC GCC CTT GTC ACC AAG CTT     288
Asp Tyr Trp Tyr Thr Trp Thr Arg Asp Ala Ala Leu Val Thr Lys Leu
    625             630             635

ATT GTC GAC GAA TTC ACC AAC GAC TAC AAC ACC ACT CTT CAG AAC ACC     336
Ile Val Asp Glu Phe Thr Asn Asp Tyr Asn Thr Thr Leu Gln Asn Thr
640             645             650             655

ATT CAG GCT TAT GCT GCT GCA CAG GCC AAG CTT CAG GGC GTT AGC AAC     384
Ile Gln Ala Tyr Ala Ala Ala Gln Ala Lys Leu Gln Gly Val Ser Asn
                660             665             670

CCG TCC GGT TCC CTC TCC AAC GGG GCC GGT CTT GGT GAG CCC AAG TTC     432
Pro Ser Gly Ser Leu Ser Asn Gly Ala Gly Leu Gly Glu Pro Lys Phe
            675             680             685

ATG GTC GAC CTC CAG CAG TTC ACC GGT GCC TGG GGC CGC CCC CAG AGG     480
Met Val Asp Leu Gln Gln Phe Thr Gly Ala Trp Gly Arg Pro Gln Arg
        690             695             700

GAT GGC CCT CCC CTT CGC GCC ATT GCC CTG ATC GGC TAT GGC AAG TGG     528
Asp Gly Pro Pro Leu Arg Ala Ile Ala Leu Ile Gly Tyr Gly Lys Trp
    705             710             715

CTC GTC AGC AAC GGT TAT GCT GAT ACG GCC AAG AGC ATC ATC TGG CCC     576
Leu Val Ser Asn Gly Tyr Ala Asp Thr Ala Lys Ser Ile Ile Trp Pro
720             725             730             735
```

FIGURE 7 B

| | |
|---|---|
| ATT GTG AAG AAC GAC CTT GCC TAC ACT GCC CAG TAC TGG AAC AAC ACT<br>Ile Val Lys Asn Asp Leu Ala Tyr Thr Ala Gln Tyr Trp Asn Asn Thr<br>　　　　　　　740　　　　　　　　　745　　　　　　　　　750 | 624 |
| GGC TTC GAT CTC TGG GAG GAG GTT AAC AGC TCT TCT TTC TTC ACC ATC<br>Gly Phe Asp Leu Trp Glu Glu Val Asn Ser Ser Ser Phe Phe Thr Ile<br>　　　　　　755　　　　　　　　　760　　　　　　　　　765 | 672 |
| GCC GCC TCC CAC CGT GCT CTC GTT GAG GGT TCT GCT TTT GCC AAG TCC<br>Ala Ala Ser His Arg Ala Leu Val Glu Gly Ser Ala Phe Ala Lys Ser<br>　　　　770　　　　　　　　　775　　　　　　　　　780 | 720 |
| GTC GGC AGC TCT TGC AGC GCT TGC GAT GCC ATT GCC CCC CAA ATT CTG<br>Val Gly Ser Ser Cys Ser Ala Cys Asp Ala Ile Ala Pro Gln Ile Leu<br>　　　785　　　　　　　　　790　　　　　　　　　795 | 768 |
| TGC TTC CAG CAG AGC TTC TGG TCC AAC AGC GGC TAC ATC ATC TCC AAC<br>Cys Phe Gln Gln Ser Phe Trp Ser Asn Ser Gly Tyr Ile Ile Ser Asn<br>800　　　　　　　　805　　　　　　　　　810　　　　　　　　　815 | 816 |
| TTT GTC AAC TAC CGC AGC GGC AAG GAC ATC AAC TCC GTC TTG ACT TCC<br>Phe Val Asn Tyr Arg Ser Gly Lys Asp Ile Asn Ser Val Leu Thr Ser<br>　　　　　　820　　　　　　　　　825　　　　　　　　　830 | 864 |
| ATC CAC AAC TTC GAC CCC GCT GCC GGT TGC GAT GTC AAC ACC TTC CAG<br>Ile His Asn Phe Asp Pro Ala Ala Gly Cys Asp Val Asn Thr Phe Gln<br>　　　　　　835　　　　　　　　　840　　　　　　　　　845 | 912 |
| CCC TGC AGC GAC CGG GCT CTT GCC AAC CAC AAG GTT GTC GTT GAC TCC<br>Pro Cys Ser Asp Arg Ala Leu Ala Asn His Lys Val Val Val Asp Ser<br>　　　　850　　　　　　　　　855　　　　　　　　　860 | 960 |
| ATG CGC TTC TGG GGT GTC AAC TCC GGT CGC ACT GCC GGT AAG GCC GCC<br>Met Arg Phe Trp Gly Val Asn Ser Gly Arg Thr Ala Gly Lys Ala Ala<br>　　　865　　　　　　　　　870　　　　　　　　　875 | 1008 |
| GCT GTC GGT CGC TAC GCT GAG GAT GTC TAC TAC AAC GGT AAC CCG TGG<br>Ala Val Gly Arg Tyr Ala Glu Asp Val Tyr Tyr Asn Gly Asn Pro Trp<br>880　　　　　　　　885　　　　　　　　　890　　　　　　　　　895 | 1056 |
| TAC CTC GCT ACT CTC GCC GCC GCC GAG CAG CTC TAC GAC GCC GTC TAC<br>Tyr Leu Ala Thr Leu Ala Ala Ala Glu Gln Leu Tyr Asp Ala Val Tyr<br>　　　　　　900　　　　　　　　　905　　　　　　　　　910 | 1104 |
| GTC TGG AAG AAG CAG GGT TCT ATC ACT GTC ACC TCC ACC TCC CTC GCC<br>Val Trp Lys Lys Gln Gly Ser Ile Thr Val Thr Ser Thr Ser Leu Ala<br>　　　　　　915　　　　　　　　　920　　　　　　　　　925 | 1152 |
| TTC TTC AAG GAC CTC GTT CCC TCC GTC AGC ACC GGC ACC TAC TCC AGC<br>Phe Phe Lys Asp Leu Val Pro Ser Val Ser Thr Gly Thr Tyr Ser Ser<br>　　　　930　　　　　　　　　935　　　　　　　　　940 | 1200 |

FIGURE 7 C

```
TCT TCC TCC ACC TAC ACC GCC ATC ATC AAC GCC GTC ACC ACC TAT GCC        1248
Ser Ser Ser Thr Tyr Thr Ala Ile Ile Asn Ala Val Thr Thr Tyr Ala
    945             950             955

GAC GGC TTC GTC GAC ATC GTT GCC CAG TAC ACT CCC TCC GAC GGC TCC        1296
Asp Gly Phe Val Asp Ile Val Ala Gln Tyr Thr Pro Ser Asp Gly Ser
960             965             970             975

CTG GCC GAG CAG TTC GAC AAG GAT TCG GGC GCC CCC CTC AGC GCC ACC        1344
Leu Ala Glu Gln Phe Asp Lys Asp Ser Gly Ala Pro Leu Ser Ala Thr
            980             985             990

CAC CTG ACC TGG TCG TAC GCC TCC TTC CTT TCC GCC GCC GCC CGC CGC        1392
His Leu Thr Trp Ser Tyr Ala Ser Phe Leu Ser Ala Ala Ala Arg Arg
        995             1000            1005

GCC GGC ATC GTC CCT CCC TCG TGG GGC GCC GCG TCC GCC AAC TCT CTG        1440
Ala Gly Ile Val Pro Pro Ser Trp Gly Ala Ala Ser Ala Asn Ser Leu
    1010            1015            1020

CCC GGT TCC TGC TCC GCC TCC ACC GTC GCC GGT TCA TAC GCC ACC GCG        1488
Pro Gly Ser Cys Ser Ala Ser Thr Val Ala Gly Ser Tyr Ala Thr Ala
    1025            1030            1035

ACT GCC ACC TCC TTT CCC GCC AAC CTC ACG CCC GCC AGC ACC ACC GTC        1536
Thr Ala Thr Ser Phe Pro Ala Asn Leu Thr Pro Ala Ser Thr Thr Val
1040            1045            1050            1055

ACC CCT CCC ACG CAG ACC GGC TGC GCC GCC GAC CAC GAG GTT TTG GTA        1584
Thr Pro Pro Thr Gln Thr Gly Cys Ala Ala Asp His Glu Val Leu Val
            1060            1065            1070

ACT TTC AAC GAA AAG GTC ACC ACC AGC TAT GGT CAG ACG GTC AAG GTC        1632
Thr Phe Asn Glu Lys Val Thr Thr Ser Tyr Gly Gln Thr Val Lys Val
            1075            1080            1085

GTC GGC AGC ATC GCT CGG CTC GGC AAC TGG GCC CCC GCC AGC GGG CTC        1680
Val Gly Ser Ile Ala Arg Leu Gly Asn Trp Ala Pro Ala Ser Gly Leu
            1090            1095            1100

ACC CTG TCG GCC AAA CAG TAC TCT TCC AGC AAC CCG CTC TGG TCC ACC        1728
Thr Leu Ser Ala Lys Gln Tyr Ser Ser Ser Asn Pro Leu Trp Ser Thr
    1105            1110            1115

ACT ATT GCG CTG CCC CAG GGC ACC TCG TTC AAG TAC AAG TAT GTC GTC        1776
Thr Ile Ala Leu Pro Gln Gly Thr Ser Phe Lys Tyr Lys Tyr Val Val
1120            1125            1130            1135

GTC AAC TCG GAT GGG TCC GTC AAG TGG GAG AAC GAT CCT GAC CGC AGC        1824
Val Asn Ser Asp Gly Ser Val Lys Trp Glu Asn Asp Pro Asp Arg Ser
            1140            1145            1150
```

FIGURE 7 D

| TAT | GCT | GTT | GGG | ACG | GAC | TGC | GCC | TCT | ACT | GCG | ACT | CTT | GAT | GAT | ACG | 1872 |
| Tyr | Ala | Val | Gly | Thr | Asp | Cys | Ala | Ser | Thr | Ala | Thr | Leu | Asp | Asp | Thr | |
|     |     |     | 1155 |     |     |     |     | 1160 |     |     |     |     | 1165 |     |     |     |

TGG AGG TAA                                                                1881
Trp Arg OCH

FIGURE 8 A

| | | | | | |
|---|---|---|---|---|---|
| AAATTGTAAA | CGTTAATATT | TTGTTAAAAT | TCGCGTTAAA | TTTTTGTTAA | ATCAGCTCAT | 60 |
| TTTTTAACCA | ATAGGCCGAA | ATCGGCAAAA | TCCCTTATAA | ATCAAAAGAA | TAGACCGAGA | 120 |
| TAGGGTTGAG | TGTTGTTCCA | GTTTGGAACA | AGAGTCCACT | ATTAAAGAAC | GTGGACTCCA | 180 |
| ACGTCAAAGG | GCGAAAAACC | GTCTATCAGG | GCGATGGCCC | ACTACGTGAA | CCATCACCCT | 240 |
| AATCAAGTTT | TTTGGGGTCG | AGGTGCCGTA | AAGCACTAAA | TCGGAACCCT | AAAGGGAGCC | 300 |
| CCCGATTTAG | AGCTTGACGG | GGAAAGCCGG | CGAACGTGGC | GAGAAAGGAA | GGGAAGAAAG | 360 |
| CGAAAGGAGC | GGGCGCTAGG | GCGCTGGCAA | GTGTAGCGGT | CACGCTGCGC | GTAACCACCA | 420 |
| CACCCGCCGC | GCTTAATGCG | CCGCTACAGG | GCGCGTCCCA | TTCGCCATTC | AGGCTACGCA | 480 |
| ACTGTTGGGA | AGGGCGATCG | GTGCGGGCCT | CTTCGCTATT | ACGCCAGCTG | GCGAAGGGGG | 540 |
| GATGTGCTGC | AAGGCGATTA | AGTTGGGTAA | CGCCAGGGTT | TTCCCAGTCA | CGACGTTGTA | 600 |
| AAACGACGGC | CAGTGAATTG | TAATACGACT | CACTATAGGG | CGAATTGAGC | TCCACCGCGG | 660 |
| TGGCGGCCGC | TCTAGCGATG | GCAGCCACCA | TTCATTTCTC | GATGCGACGG | TAAACGACGC | 720 |
| CCGCGGCAGA | TTAGGTCATT | GCCGAACGGA | TTGAAGCTCT | CTCCATCTTG | GATCCATTCC | 780 |
| CGGCCAATCC | CGTCTCGGCC | AACCACACTG | TCCACTCGCC | CAGGTCAGCA | GCTCAGGACT | 840 |
| CTCTCCTGGT | TTGGTACCGC | TTAGTGTAGA | GCATACCGCT | CTCAGTCCCC | ATAGACCAAC | 900 |
| CATAACACCG | CACGTTCTCT | TTCACTCAAG | ATGCTTATCA | TGTCCCCTCT | TTCTGCTCCA | 960 |
| ATGATTCGGA | CTGGTCGAAT | ACCAATGAGA | CAAGCGAGAG | CGCAGTGCGA | GCAAGCGTTC | 1020 |
| CTGCAGATAG | AGCAGTGGGA | CTGCCGCGCC | ACAAAGGAAG | AGGATCGTGA | CGTGACGTGA | 1080 |
| CCAGTGACCA | GAAAGCAGAA | GATCCAAAAG | AGTCAAAAGG | ACCGAGCCTC | ACCTACAGTA | 1140 |
| ATGGCCCGGA | TGGCACTCAA | GACCGTCCTC | TCGGCCCTTT | CTCCAACTCT | TCTCCTTCCA | 1200 |
| TAATTCACCT | AGGTACATAC | ACGGCCTACG | CTTCCGCCTC | ATCCATCCC | ATCCATCCC | 1260 |
| ATCCCATCCC | ATCGACGACT | CTAACCCGCC | CGCGAGTGCA | AACCTCGTCC | ACGAACGGAC | 1320 |
| ACCCCGGCTC | TCCTCCGAAG | CCCTTGCAAG | TGGAAGCTGA | GGTTGCCGAA | CTTAGACGAC | 1380 |
| CAGGTTCACC | AGCCGGACCG | CAACTCGAAC | GTCAGAATAC | AGCCTCAGCC | TCCAAAGGGG | 1440 |
| GTTAACGCCA | AGCGAGAGCA | AGACAAGATC | GTCGCCCATC | AATATCCTGG | ACAAGACAAC | 1500 |

FIGURE 8 B

```
ATGGACGCAA TATATAACCT CAAGCAAGTC CTCCTCAGCA ACCATGATTT CACCACCAGC    1560

CTGGTCTCCA ACGCAACAGA CTTCTCGACA AGTCCCTTGA CCTACTTCGC CATGCATCTC    1620

GTCTCTTCGC TCCTCGTCGT GGGCGCCGCC TTCCAGGCCG TGCTCGGTCT GCCGGATCCT    1680

CTGCATGAAA AGAGGCACAG CGACATCATC AAGCGGTCTG TCGACCGGAC GCGCCCCCGG    1740

GTTAATTAAG TCTAGAGTGG AGGTAAATCG CTTGCTTCGT ACTAGGTAGT AAGTAGTGAT    1800

TGGGAAAAGG AAATGAGAGA ACGGGAACGG GAACGGGAAC GGGAATTTGT GATTACAAAG    1860

TGTAAAATTA ATAGGCCCGG GATTTTGGTT AGATGCATAA GGGGGGCAGG GGGGGCTAGG    1920

AAACGGAAGG TTGCATATCA ACCGAGGAAG AATGGGAAGA AAGGGAAGAA AGACAGAAAG    1980

AAGGAACAAC AGGACTTCAT TCTCTCACAT CGACATGAGC TACCTGGGCA TCAGCTACCT    2040

GGGCATCTTG ATTTCCTTTT TAGAAGATTG TTTTGTATCC TTTTTTCTTC CTCCCTTTTC    2100

TTTTCTTGTC CGTCTCTTAC ACCTACCTAT TTTTAGCCAA AGTCCACACA CACACAAACT    2160

TTTTGTTAGA TATTCTCTGT ATCAAAATTG ACAAGTTTCA ATGTTATACA GTACCTTGCC    2220

AAGTTTAATA CACATTCAAA TCAATCAACC ACACACACAC AAGTTTTATT GTGCAGAAAT    2280

GGAGTGAAGA AGAAACATGT TTGGGATTAT GATGACAAGC TTCTCAACAA AATTTCAACG    2340

AGTTAAGCTT CAAAGGTCCG CTGGCTCAAT GGCAGAGCGT CTGACTACGA ATCAGGAGGT    2400

TCCAGGTTCG ACCCCTGGGT GGATCGAGTT GCAAATTGGT ACTTTGAGTA CCAAAGTTCC    2460

TTTTTTTTTT TCGTTTGGCT CTCTGCTTTT CGACAGTTCA CTGAGTCATG TGCAAGACAC    2520

CCCTGATCGG GTACGTACTG AACTGCTTTT GGTGCAGTGC AATGGTTCTC GAGGGGGGGC    2580

CCGGTACCCA GCTTTTGTTC CCTTTAGTGA GGGTTAATTC CGAGCTTGGC GTAATCATGG    2640

TCATAGCTGT TTCCTGTGTG AAATTGTTAT CCGCTCACAA TTCCACACAA CATAGGAGCC    2700

GGAAGCATAA AGTGTAAAGC CTGGGGTGCC TAATGAGTGA GGTAACTCAC ATTAATTGCG    2760

TTGCGCTCAC TGCCCGCTTT CCAGTCGGGA AACCTGTCGT GCCAGCTGCA TTAATGAATC    2820

GGCCAACGCG CGGGGAGAGG CGGTTTGCGT ATTGGGCGCT CTTCCGCTTC CTCGCTCACT    2880

GACTCGCTGC GCTCGGTCGT TCGGCTGCGG CGAGCGGTAT CAGCTCACTC AAAGGCGGTA    2940

ATACGGTTAT CCACAGAATC AGGGGATAAC GCAGGAAAGA ACATGTGAGC AAAAGGCCAG    3000

CAAAAGGCCA GGAACCGTAA AAAGGCCGCG TTGCTGGCGT TTTTCCATAG GCTCGGCCCC    3060

CCTGACGAGC ATCACAAAAA TCGACGCTCA AGTCAGAGGT GGCGAAACCC GACAGGACTA    3120
```

FIGURE 8 C

```
TAAAGATACC AGGCGTTCCC CCCTGGAAGC TCCCTCGTGC GCTCTCCTGT TCCGACCCTG    3180
CCGCTTACCG GATACCTGTC CGCCTTTCTC CCTTCGGGAA GCGTGGCGCT TTCTCAATGC    3240
TCACGCTGTA GGTATCTCAG TTCGGTGTAG GTCGTTCGCT CCAAGCTGGG CTGTGTGCAC    3300
GAACCCCCCG TTCAGCCCGA CCGCTGCGCC TTATCCGGTA ACTATCGTCT TGAGTCCAAC    3360
CCGGTAAGAC ACGACTTATC GCCACTGGCA GCAGCCACTG GTAACAGGAT TAGCAGAGCG    3420
AGGTATGTAG GCGGTGCTAC AGAGTTCTTG AAGTGGTGGC CTAACTACGG CTACACTAGA    3480
AGGACAGTAT TTGGTATCTG CGCTCTGCTG AAGCCAGTTA CCTTCGGAAA AAGAGTTGGT    3540
AGCTCTTGAT CCGGCAAACA AACCACCGCT GGTAGCGGTG GTTTTTTTGT TTGCAAGCAG    3600
CAGATTACGC GCAGAAAAAA AGGATCTCAA GAAGATCCTT TGATCTTTTC TACGGGGTCT    3660
GACGCTCAGT GGAACGAAAA CTCACGTTAA GGGATTTTGG TCATGAGATT ATCAAAAAGG    3720
ATCTTCACCT AGATCCTTTT AAATTAAAAA TGAAGTTTTA AATCAATCTA AGTATATAT     3780
GAGTAAACTT GGTCTGACAG TTACCAATGC TTAATCAGTG AGGCACCTAT CTCAGCGATC    3840
TGTCTATTTC GTTCATCCAT AGTTGCCTGA CTGCCCGTCG TGTAGATAAC TACGATACGG    3900
GAGGGCTTAC CATCTGGCCC CAGTGCTGCA ATGATACCGC GAGACCCACG CTCACCGGCT    3960
CCAGATTTAT CAGCAATAAA CCAGCCAGCC GGAAGGGCCG AGCGCAGAAG TGGTCCTGCA    4020
ACTTTATCCG CCTCCATCCA GTCTATTAAT TGTTGCCGGG AAGCTAGAGT AAGTAGTTCG    4080
CCAGTTAATA GTTTGCGCAA CGTTGTTGCC ATTGCTACAG GCATCGTGGT GTCACGCTCG    4140
TCGTTTGGTA TGGCTTCATT CAGCTCCGGT TCCCAACGAT CAAGGCGAGT TACATGATCC    4200
CCCATGTTGT GAAAAAAAGC GGTTAGCTCC TTCGGTCCTC CGATCGTTGT CAGAAGTAAG    4260
TTGGCCGCAG TGTTATCACT CATGCTTATG GCAGCACTGC ATAATTCTCT TACTGTCATG    4320
CCATCCGTAA GATGCTTTTC TGTGACTGGT GAGTACTCAA CCAAGTCATT CTGAGAATAG    4380
TGTATGCGGC GACCGAGTTG CTCTTGCCCG GCGTCAATAC GGGATAATAC CGCGCCACAT    4440
AGCAGAACTT TAAAAGTGCT CATCATTGGA AAACGTTCTT CGGGGCGAAA ACTCTCAAGG    4500
ATCTTACCGC TGTTGAGATC CAGTTCGATG TAACCCACTC GTGCACCCAA CTGATCTTCA    4560
GCATCTTTTA CTTTCACCAG CGTTTCTGGG TGAGCAAAAA CAGGAAGGCA AAATGCCGCA    4620
AAAAAGGGAA TAAGGGCGAC ACGGAAATGT TGAATACTCA TACTCTTCCT TTTTCAATAT    4680
```

FIGURE 8 D

```
TATTGAAGCA TTTATCAGGG TTATTGTCTC ATGAGCGGAT ACATATTTGA ATGTATTTAG    4740

AAAAATAAAC AAATAGGGGT TCCGCGCACA TTTCCCCGAA AAGTGCCACC TG            4792
```

PRODUCTION OF HETEROLOGOUS PEPTIDES

The invention relates to a method and recombinant means particularly, but not exclusively, expression cassettes and expression/export cassettes for the production of heterologous peptides. The method and means have particular application in the production of such peptides from the biotechnological exploitation of filamentous fungi and particularly Neurospora crassa.

The filamentous fungi secrete substantial amounts of protein, notably hydrolytic enzymes. Many of these enzymes are used in industrial processes such as the production of antibiotics and organic acids, the saccharification of starch, glucose isomerisation, the processing of wines and fruit juices and the degradation of cellulose and lignin (Bennett 1985; Bu'Lock and Kristiansen 1987). The promoter and signal sequences of the genes of such enzymes represent targets for manipulation for developing the filamentous fungi as hosts for heterologous gene expression. The potential for this technology has been reviewed with particular reference to the genus Aspergillus (Van den Hondel et al 1991).

The term heterologous gene expression is used in this document to mean the expression of genes not present or common in the host.

The genus Neurospora has several advantages for study with a view to its possible exploitation as a host for heterologous gene expression.

More specifically, the species Neurospora crassa is the most thoroughly studied and characterised of all the filamentous fungi (Reviewed by Perkins DD [1992] genetics 130:687–700), with more genes characterised and more genes cloned than any other species. It is extremely fast-growing, with simple growth requirement. It will grow on a wide range of carbon and nitrogen sources, and has a single complex growth requirement, for biotin. It will grow in liquid or on solid medium. It produces no toxic secondary metabolities, and in fact is a traditional oriental human food organism.

Neurospora in nature grows in a solid medium, and has efficient secreted enzyme systems for the utilisation of polysaccharide carbon sources. These include glucoamylase, the major exported protein when starch-induced. Secreted proteins in wide-type Neurospora reach levels of circa 1 g/l of spent medium, the glucoamylase, when starch-induced, accounts for circa 20% of the total. For glucoamylase, there is evidence for two regulatory components, carbon catabolite repression, and induction by the substrate or some partial hydrolysis product of such.

Glucoamylases have been cloned and characterised from several fungi: Aspergillus awamori (Nunberg et al 1984), A. awamonri var. kawachi (Hayashida et al 1989) A. niger (Boel et al 1984), A oryzae (Hata et al 1991), A. shirousami (Shibuya et al 1990), Humicola grisea var. thermoidea (Berka et al, personal communication), Rhizopus oryzae (Ashikari et al 1986), Saccharaomyces cerevisiae (Pardo et al 1988), S. diastaticus (Yamashita et al 1985), S. fibuligera (d, (Itoh et al 1987), and S. occidentalis (Dohmen et al 1990).

Glucoamylases (exo-1,4-x-D-glucan glucohydrolase, EC 3.2.1.3) are secreted in large amounts by a variety of filamentous fungi. They catalyse the removal of single glucose units from the non-reducing ends of starch and other poly- and oligo-saccharides. Their use in industrial processes includes the production of glucose syrups from starch (Kennedy et al 1988), and the fermentation of sake, (rice wine) in Japan. Heterologous expression systems in the above Aspergillus species of filamentous fungi commonly use their glucoamylase promoters to drive expression, their signal sequences to secrete foreign peptides, and their 3' flanking regions to direct termination (Archer et al 1990; Ward et at 1990, 1992).

Koh-Luar et al (1989) analysed culture supernatans of Neurospora crassa, growing on a variety of carbon sources, and showed that the protein present in the largest amount was a glucoamylase of approximately 69 kDa. This protein was purified and the N-terminal sequence of the glucoamylase determined.

The high expression and secretion properties of the Glucoamylase gene makes it an attractive candidate for use in heterologous gene expression. The glucoamylase promoter can be used independent of the glucoamylase open reading frame so exploiting the promoter's high transcription levels as well as the regulation in response to extracellular carbon. The highly secreted open reading frame of the glucoamylase gene can be used in conjunction with the glucoamylase promoter to target foreign proteins into the secretory pathway of Neurospora crassa. In this case, the entire open reading frame or a portion of the glucoamylase gene can be attached in frame to the foreign gene.

Here we report the DNA sequence of the glucoamylase gene, gla-1, of Neurospora crassa together with flanking sequences and compare its amino-acid sequence with other glucoamylases.

Having obtained the DNA sequence structure of the aforementioned gene, we have characterised an unexpectedly very high level, regulated promoter, and determined key features of its carbon catabolite repression and its induction by a polysaccharide substrate such as starch or metabolites thereof. With this information, we are in a position to genetically engineer expression cassettes and expression/export cassettes containing this high level regulated promoter along with any other pre-selected peptide. The control of production of this peptide is in accordance with the repression and induction features of the promoter. Thus, we can selectively control the production of the peptide according to the presence or absence of carbon catabolite.

It is apparent that this technology has great significance in the genetic engineering industry because it enables selective production of a pre-determined peptide in am extremely efficient and cost effective way without the production of secondary metabolites. Further, since Neurospora, like other filamentous ascomycete fungi but unlike yeasts, tends to glycosylate proteins in a way resembling that of mammals, there is reasonable expectation that any heterologously produced mammalian peptide sequences requiring glycosylation for biological activity will in fact be biologically active.

In addition, Neurospora, can be transformed at high efficiency, with transformed sequences being integrated, at least vegetatively stably, generally into heterologous locations in the genome.

Further, we also report here modifications of the glucoamylase coding region which improves the gene's utility as a vector for heterologous gene expression.

According to a first aspect of the invention there is therefore provided a regulated promoter having the DNA sequence structure shown in FIG. 1, or part thereof, of a functionally equivalent nucleotide sequence.

According to a second aspect of the invention there is provided a regulated promoter and an upstream activator having the DNA sequence structure shown in FIG. 1, or part thereof, and especially having the sequence structure shown in the first one thousand nucleotides of the DNA sequence structure shown in FIG. 1, or part thereof.

Preferably the DNA sequence structure shown in FIG. 1 encodes a protein the amino acid sequence of which is depicted in FIG. 1 or a protein of equivalent biological activity, having substantially the amino acid sequence depicted in FIG. 1.

It follows that since the DNA sequence structure shown in FIG. 1 encodes the protein glucoamylase then the regulated promoter of the invention is the promoter controlling the expression of the glucoamylase gene.

According to a third aspect of the invention there is provided a regulated promoter as aforedescribed which is further provided with linkers whereby ligation of the promoter with a pre-selected gene encoding a desired protein is facilitated.

According to a yet further aspect of the invention there is provided a vector or plasmid (pPS8) incorporating the aforementioned DNA sequence structure.

Preferably said vector or plasmid incorporates a 904 nucleotide fragment of said DNA sequence structure located between a BamH1 site at nucleotide 98 and a HindIII site at nucleotide 1002.

According to a yet further aspect of the invention there is provided an expression cassette including at least the aforementioned regulated promoter DNA sequence and a pre-selected gene encoding a heterologous peptide.

Preferably the expression cassette also includes the upstream activator sequence.

Preferably further still said expression cassette includes a marker selectable in Neurospora which ideally is a gene encoding hygromycin-resistance.

Preferably further still said expression cassette contains a replication origin from, ideally, *E. coli* and preferably also an *E. coli*-selectable marker, for example a gene encoding ampicillin-resistance.

Preferably further still said expression cassette incorporates a multi-cloning site whereby the insertion of any pre-selected gene sequence can be incorporated via transcriptional fusion.

According to a yet further aspect of the invention there is provided an expression/export cassette which incorporates any one or combination of the aforementioned expression features and which further incorporates a DNA sequence structure encoding a secretion signal.

Preferably said expression/export cassette contains the aforementioned DNA sequence translationally fused to the coding sequence for the heterologous peptide.

Preferably three different expression/export cassettes are provided. The multiple cloning site oligonucleotide is in a different reading frame in each to permit in-frame translational fusion to the coding sequence for the heterologous peptide. This is achieved by appropriate design of the ends of the synthetic multiple cloning site oligonucleotide.

It will be apparent to those skilled in the art that the provision of an expression/export cassette enables a heterologous peptide to be both expressed and then exported into culture medium, however, this limits the range of peptides which can be made but the advantage is that it facilitates the purification of those peptides that can be made using this method.

In preferred embodiments of the invention the selected heterologous peptide is a medical or pharmaceutical peptide such as insulin, human growth hormone, interleukin or indeed any other suitable peptide.

According to a yet further aspect of the invention there is provided expressions cassettes and/or expression/export cassettes, also referred to as constructs or plasmids as described hereinafter for enabling the working of the invention.

In a preferred embodiment of the invention there is provided the plasmid pGla-Xho I as illustrated in FIG. 3.

In yet a further embodiment of the invention there is provided the plasmid Gla-Mro as illustrated in FIG. 5.

In yet a further preferred embodiment of the invention there is provided the plasmid pGE as illustrated in FIG. 6.

In yet a preferred embodiment of the invention there is provided the plasmid pGS as illustrated in FIG. 8.

Further preferred constructs or plasmids of the invention include those plasmids which could be termed intermediary and which are used either in isolation or combination to provide the abovementioned plasmids, for example, intermediary constructs include the plasmids pGla XL-,pGIA XLX, and pGla MXL used to manufacture the construct pGE and other intermediary constructs include pGla XhoI used to manufacture construct pGS.

According to a yet further aspect of the invention there is provided primers for manufacturing the constructs or plasmids hereindescribed which primers are shown in FIG. 4.

It will apparent to those skilled in the art that shorter primer sequences may be used in order to work the invention or that substitutions of one or more bases within the primers described in FIG. 4 may be used providing hybridisation can be achieved. Thus it follows that shorter primer sequences or sequences with minor internal base substitutions may be used to work the invention and can easily be tested for this purpose using the methods described herein.

According to a yet further aspect of the invention there is provided a method for transforming filamentous fungus comprising the insertion of at least one of the aforementioned expression cassettes and/or export/expression cassettes into same using recombinant techniques.

In a preferred embodiment of the invention said filamentous fungus is *Neurospora crassa*.

According to a yet further aspect of the invention there is provided a filamentous fungus including at least one expression cassette and/or expression/export cassette according to the invention.

Preferably said filamentous fungus is *Neurospora crassa*.

According to a yet further aspect of the invention there is provided a method fox the production of a pre-selected heterologous peptide from at least one filamentous fungus comprising:

a) providing either an expression cassette or an expression/export cassette as aforedescribed.

b) transforming a pre-selected species of filamentous fungus with at least one of said cassettes.

c) culturing said transformed fungus; and d) harvesting said heterologous peptide.

The invention will now be described, by way of example only, with reference to the following figures wherein.

BRIEF DESCRIPTION OF THE FIGURES

FIG. 1 SEQ ID NO:6 shows the DNA sequence structure of the glucoamylase gene and the corresponding amino acid sequence structure of the protein glucoamylase. The glucoamylase reading frame is shown in upper case, together with its translation below. Untranslated regions are shown in lower case. The numbering for the nucleotides is based on the A of the ATG being +1. The numbering for the amino acids are in brackets. The putative promoter elements are underlined in bold. The functional domains of the intron are in bold. The leader sequence of the protein is in bold, with the signal splice shown as an arrow. The Lys-Arg (Kex2) propeptide processing sites are underlined. The putative polyadenylation signal is also underlined in bold.

FIG. 3 SEQ ID NO: 3 shows the DNA sequence structure of the plasmid pGla-Xho I.

FIG. 4 shows SEQ ID NO:8, 10, 11, 12, 13 the primers used for the creation of the Mro I site at the final codon of the glucoamylase gene.

FIG. 5 SEQ ID NO:5 shows the DNA sequence structure of the plasmid pGla-Mro.

FIG. 6 SEQ ID NO:2 shows the DNA sequence structure of the plasmid pGE.

FIG. 7 SEQ ID NO:4,7 shows the relative location of the Sal I site to the second Kex-2 site in the glucoamylase gene.

FIG. 8 SEQ ID NO:1 shows the DNA sequence structure of the plasmid pGS; and

Cloning of the Glucoamylase Gene

The Neurospora glucoamylase gene gla-1 was cloned and sequenced by conventional methods such as sequence alignment of the gene from other species, design of nested PCR primers, and production of a fragment by PCR which was used to identify a genomic clone from a Neurospora genomic library in the vector lambda J1. The clone was sub-cloned into pBluescript, and sequenced by the Sanger-dideoxy method.

The genes encodes the deduced protein of 626 amino acids, with unglycosylated molecular weight of 66, 575 Da. This includes a leader peptide of 35 amino acids when compared to the known N-terminus of the secreted protein.

We have sequenced 938 base pairs upstream of the translation initiation codon. There is a TATA box at position -101 with respect to the ATG codon. The actual sequence is TATATAA and the eukaryotic consensus TATA(A/T)TA. There are several potential, although no perfect, CAAT boxes upstream of the TATA box, the most likely one to function being at -133 to the ATG start codon (CATCAATAT). The eukaryotic consensus sequence is GG(C/T)CAATCT.

The initiation points of translation have been shown to have a very strong requirement for a purine at position -3 with respect to the initiating AUG.

Isolation of the Essential Promoter Region

The promoter, regulatory regions, and probably also any UAS (upstream activator sequences) are contained in the first 938 nucleotides of the determined sequence. This, together with the rest of the clone, is contained in our plasmid pPS8. A 904 nucleotide fragment between a BamH1 site at nucleotide 98 and a HindIII site at nucleotide 1002 containing the major part of the promoter, and the N-terminal major part of the signal peptide of the gene product may be readily sub-cloned and tested for promoter and starch-regulatory activity with a suitable reporter gene.

A suitable restriction site at nucleotide 1002 was identified in the N-terminal part of the open reading frame of the gene, and suitable constructs were made using a reporter gene so as to study promoter activity and regulator functions as described below.

Plasmid pPS8

Figure 2:
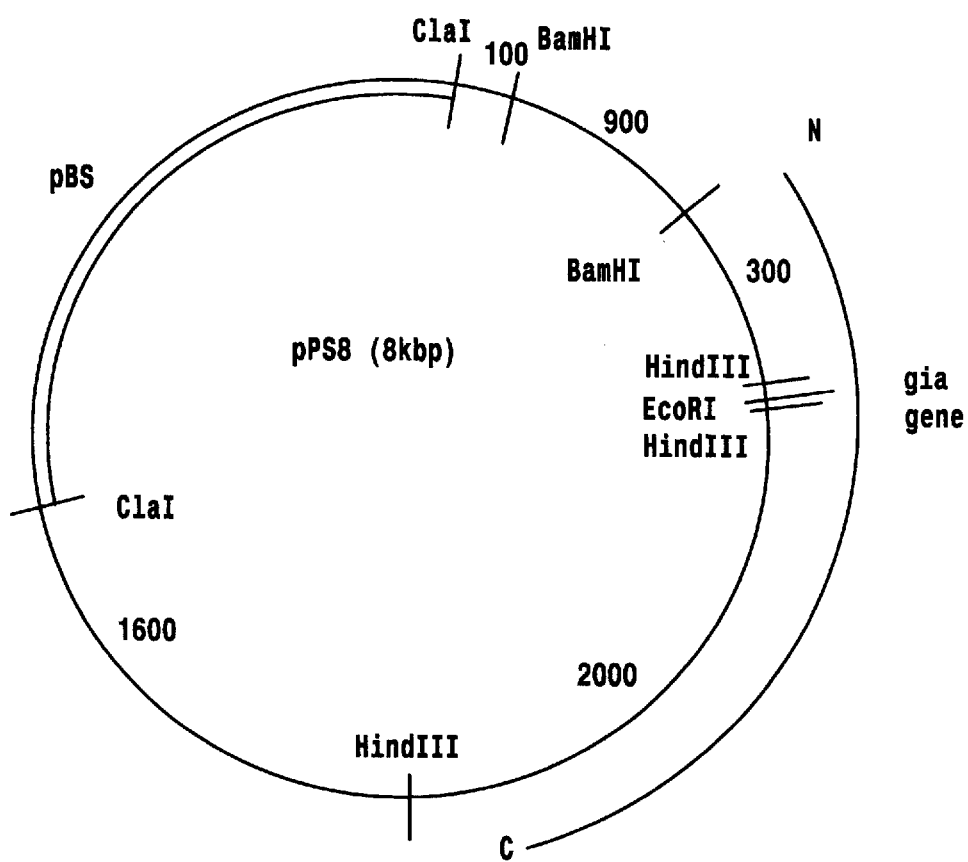
FIG. 2 is an illustration of plasmid pPS8.

FIG. 2 is a diagram of the pPS8 plasmid. The circa 2 kb portion in the upper left between the two ClaI sites, indicated by the double line, is the vector, pbluescript. The construct results from cleaving pbluescript at the single CLaI site, in its multiple cloning site and inserting the Neurospora ClaI fragment containing the glucoamylase gene. The outer arc labelled gla gene indicates the approximate position of the coding region of the gene, extending from N- to C-terminus. The promoter region is in the circa 1 kb upstream region between the ClaI site at 12 o'clock and the N-terminus of the coding region. The numbers indicate the approximate sizes of restriction fragments in nucleotide pairs. The restriction sites for BamH1, HindIII and EcoR1 are shown in the Neurospora insert for reference.

Choice of Reporter Gene

Two obvious choices of reporter gene exist. The first of these is the well-characterised GUS (B-glucuronidase) reporter gene available in the plasmid pNom123. This has the hph hygromycin-resistance gene as its Neurospora-selectable marker. An Alternative reporter gene is the Neurospora tyr tyrosinase construct pTry103.

Isolation of the Essential Sequence of the Promoter

Certain promoter features have already been identified by sequence homology. These include a putative CAAT box at nucleotide 804–812 (actual sequence CATCAATAT) and a TATA box at nucleotide 838–844 (actual sequence TATATAA), because of their resemblance to consensus sequences for these promoter features. Another feature identified by homology with the promoter sequence of the Aspergillus a-amylase, is the region nucleotide 301–340 of the Neurospora gla-1 sequence, with circa 75% sequence homology. This may be a UAS, or other essential feature. Two transcription origins have also been identified by primer extension, at nucleotide 885 and at nucleotide 892.

Experimental investigation of the limits of the essential promoter were undertaken by the cleavage of the sub-cloned promoter-reporter gene construct, and the deletion in from the 5'-end of the sub-clone. This involves either deletion of specific restriction fragments, subject to available restriction sites, or exonuclease degradation. In either case, the shortened "promoter" is religated into the reported construct and tested for residual promoter activity and regulation.

Experimental investigation of the limits of the essential promoter were undertaken by the cleavage of the sub-cloned promoter-reporter gene construct and the deletion in from the 5'-end of the sub-clone. This was done using mung bean exonuclease digestion. Alternatively, it could be done using any suitable restriction sites so as to provide a nested set of deletions. These deletions, or shortened promoter sequences, were religated into a reporter construct and tested for residual promoter activity and regulation.

Construction of an Expression Cassette

Deposits of plasmids pGLA-Xho, pGLA-Mro I, pGE have been made and the deposition details are as follows: pGLA-Xho1, ATCC deposition designation 75858; pGLA-Mro 1, ATCC deposition designation 75859; and pGE, ATCC deposition designation 75860.

All DNA modifying enzymes were bought from Boehringer Mannheim of New England Biolab. Plasmids were transformed into DH-5a,E.coli cells.

Modifications of the glucoamylase gene for use in targeting foreign protein into the endoplasmic reticulum required the insertion of a convenient restriction site in the open reading frame of the glucoamylase gene, and more preferably the restriction site was located at the last codon of the open reading frame of the glucoamylase gene. The restriction site tggcca, recognised by the restriction enzymes Mro I sold by Boehringer Mannheim and BspE I sold by New England Biolabs was, in the first instance, placed at the last codon of the glucoamylase gene. The restriction site tggcca will be referred to hereinafter as Mro I. In order to engineer the Mro I site, PCR primers were created. The 5' primer encompassed the unique Ppum I site at position 2163 of the glucoamylase open reading frame (see FIG. 3 SEQ ID NO:3). The 30 primer containing an Mro I site hybridizes at the 3' end of the gla gene (see FIG. 4 SEQ ID NO:12, 13).

The glucoamylase with the Mro I site was created in a two step procedure.

1. The 5'upstream PCR fragment was amplified and cloned into the Sma I site in a pNEB 193 vector. The PCR fragment was orientated so the 5' Ppum I site was proximal to the Eco RI site on the polylinker of pNEB 193. The proper clone was named pMro.

pMro: Eco Sac, Ppum I PCR Mro I Asc I, Xba I, Hind III

2. Next, the remainder of the gLa gene was inserted by digestion of the glucoamylase clone pGla-Xho I, this plasmid pGla-Xho I, contains the entire gla gene however, the downstream unsequenced and non-transcribed area was deleted. pGla-Xho I was digested with the restriction enzymes Sac I and Ppum I. This fragment was ligated into the Sac I/Ppum I sites of pMro I. The Sac I site of pGla-Xho I was derived from the linker and not from the coding region of glucoamylase consequently, no glucoamylase sequence was deleted (see FIG. 5).

pGla-Mro: Sac, Gla I Ppum I Mro, Asc I ect.

The glucoamylase gene transcribes a message of 1943. bases, not included the poly-adenylation sites. The expression construct when fused to a CDNA to be expressed, will require the transcription of a longer message. The larger open reading frame may be transcribed less efficiently than the original, shorter construct. In an attempt to increase transcription efficiency we deleted 1575 bp from the glucoamylase open reading frame, creating the plasmid pGE: (plasmid Glucoamylase, Eco RI see FIG. 6 SEQ ID NO:2).

1. The construct, pGla-Xho was digested with Cla I and Xba I and the sticky ends made blunt with *E.coli* polymerase I Klenow fragment) to remove the 5' polylinker. The DNA was then recircularised and transformed into competent *E.coli* cell DH 5a. We named this construct pGa XL-.

2. We next added a Xba I linker at the Bsa AI site in the glucoamylase gene. The Bsa AI site at position 3542 in the construct pGla XL- is thirteen base pairs away from the termination codon of glucoamylase. Complete digestion with Bsa AI would produce three fragments, consequently, a partial digest of pGla XL- with Bsa AI was performed. A linearised band corresponding to the size of pGla XL- was gel purified. Added to the gel purified fragment was 200 ng of an 8 bp Xba I linker and 400 units of T4 ligase. Clones were screened for insertion of the Xba I linker into the Bsa AI site at position 3542. Properly identified clones were renamed pGla XLX.

3. The clone pMro (described above) was digested with Ppum I and Xba I. the released fragment was ligated into pGla XLX at the Ppum I/Xba I sites. The correct clone was identified by restriction digest and renamed pGLA MAX.

4. The clone pGla MXLX was then digested with Eco RI and Mro I releasing 1575 bp of the glucoamylase open reading frame. The sticky ends were made blunt by filling in with *E.coli* polymerase I (Klenow fragment). The new expression construct was renamed pGE (plasmid Glucoamylase, Eco RI, see FIG. 6 SEQ ID NO:2). This construct contains the fusion site for glucoamylase targeting at the Eco RI site in the glucoamylase gene, 359 bp from the glucoamylase start codon We made a second glucoamylase truncated fusion expression cassette. This construct contains the fusion junction at the first Sal I site in the glucoamylase open reading frame, as position 1133 in pGla XhoI (see FIG. 1 SEQ ID NO:6). The Sal I site was chosen because it occurs immediately after the second kex-2 site at $Lys_{34}$-$Arg_{35}$ (see FIG. 5). Kex-2 sites are found in many fungal systems as proteolytic cleavage sites for removal of propeptides (reviewed in Stone et al 1993).

1. The clone pGla MXLX was digested with the restriction enzymes Sal I and Mro I. The sticky ends were made blunt with *E.coli* DNA polymerase I (Klenow fragment). The digested DNA was ligated together with 400 units of T4 DNA ligase. The proper clone was identified by restriction analysis. The clone was named pGS (plasmid Glucoamylase, Sal I), see FIG. 8.

Transformation into Neurospora

Standard transformation methodology was used to effect the transformation of DNA constructs into Neurospora spheroplasts, using the cell wall-degrading enzyme Novozym 234 (Radford et al [1981] Molec Gene Genet 184, 567–569).

DSPA Production

The glucoamylase expression vectors were used to express a mammalian thrombolytic protein secreted from the salivary glands of the vampire bat *Desmonas sauvaris*. The protein DSPA (*Desmonas salivaris* plasminogen activator) is an anti-coagulant, binding to fibrin activating the endogenous plasminogen, leading to fibrin degradation. The cDNA of DSPA was given to us by Berlix Biosciences Brisbane, Calif. for research purposes.

We have engineered the DSPA clone into a variety of vectors. With the glucoamylase vectors, we have replaced the 5' DSPA signal sequence with a Mro I site to facilitate cloning into the expression pGla-Mro and pGE. Following the Mro I site, we placed a kex-2 proteolytic site to remove the glucoamylase protein from DSPA. The expression vectors were co-transformed with a selectable marker into competent *Neurospora crassa* spheroplasts.

Figure 9:
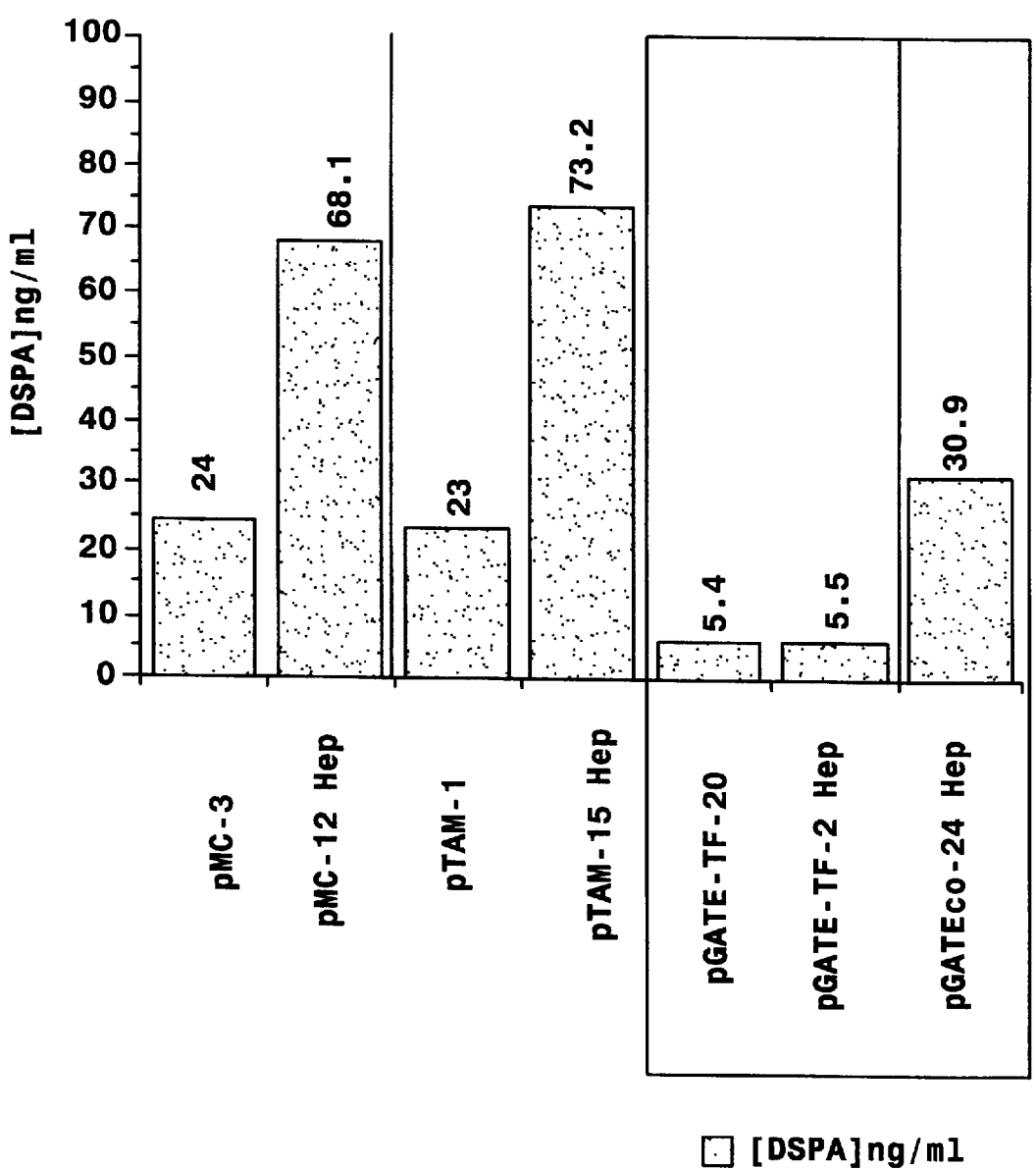
FIG. 9 shows the highest yields of DSPA from all the expression vectors tested.

In FIG. 9 we see the levels of DSPA produced by several expression vectors. The samples in the boxed area represent the levels of DSPA produced by the glucoamylase vectors. pGATE-TF contains the DSPA gene as a total fusion protein in the expression vector pGla-Mro. pGATEco, has the DSPA gene fused to the truncated glucoamylase vector pGE.

Selection of Transformants

Transformants were selected for pNom123 (the GUS reporter gene) by initial selection for hygromycin-resistance. Expression of the GUS activity was detected in a subsequent step by the development of blue colour on X-gluc substrate.

With pTyr103, the derived plasmids with putative promoter inserts have no independent selectable marker. They were co-transformed with a second plasmid with a selectable marker, a process which gives circa 50% co-integration of the unselected plasmid. Although a number of co-selectable plasmids are suitable, an example would be pFB6 (Buxton and Radford [1984] Molec Gene Genet 190, 403–405), containing the cloned pyri-4 gene of Neurospora, selecting transformants by complementation of a pyrimidine-requiring recipient strain. Transformants thus selected demonstrated promoter activity from the gla-1 promoter region by expression of tyrosinase activity in vegetative culture, tyrosinase only normally being active in the sexual phase of the life cycle. Tyrosinase activity is again detected colourmetrically, by the conversion of supplied L-tyrosine to black melanin pigment, or of L-DOPA to a soluble red pigment.

The red colour from L-DOPA, and the blue colour from X-gluc are both quantitively assayable.

Types of Product

This process would be suitable for the expression in Neurospora, and fermentor-scale production, of a wide range of peptide products, especially suited for those mammalian peptides requiring glycosylation for biological activity. It would be particularly appropriate for production of high value medical and pharmaceutical peptides, eg insulin, human growth hormone, interleukin, etc.

Method of Production

Neurospora grows well in large-scale fermentation conditions, in either aerated liquid fermentors or in solid state fermentations. It grows on a wide range, of cheap carbon and nitrogen sources, and has a complex requirement for only biotin and that in minuscule amounts.

Regulation of Production

The glucoamylase gene, and hence its promoter, is inducible by starch or maltose, and repressible by glucose. Glucoamylase is the major exported protein in Neurospora when suitably induced (Koh-Laur et al [1989] Enz Microb Technol 11). The derived expression and expression/export cassettes may be designed to have or not have such regulation. For certain recombinant products, constitutive production may be desirable, and cassettes without regulatory sequences would be used. For other recombinant products, a short induced expression phase might be advantageous or desirable. In such a case, production could be repressed initially by growth on glucose as carbon source during log-phase growth of biomass (mycelium), after which exhaustion or removal or glucose and addition of an inducing carbon source (starch or maltose) would lead to an induced expression phase.

In Summary

We have modified the glucoamylase gene of *Neurospora crassa* to improve its utility as a vector for heterologous gene expression. We have added a convenient restriction site at the last codon of the glucoamylase gene open reading frame to create a total fusion expression construct pGla-Mro I (see FIG. 3 SEQ ID NO:3). Further, we have reduced the transcript size for glucoamylase expression by deleting 1575 base pairs of the glucoaxmylase gene open reading frame so creating the plasmid pGE (see FIG. 6 SEQ ID NO:2). In addition we engineered a restriction site 13 base pairs from the termination codon of glucoamylase to place the cDNA of interest proximal to the polyadenalation site of the glucoamylase gene. Finally we have created an expression cassette containing the glucoamylase signal, propeptide and polyadenalation sites. This expression cassette is plasmid pGS (see FIG. 8 SEQ ID NO:1).

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
  ( A ) LENGTH: 5042 base pairs
  ( B ) TYPE: nucleic acid
  ( C ) STRANDEDNESS: double
  ( D ) TOPOLOGY: circular ( i i ) MOLECULE TYPE: other nucleic acid
  ( A ) DESCRIPTION: /desc = "Plasmid pGE"

( x i ) SEQUENCE DESCRIPTION: SEQ ID NO: 1:

| | | | | | | |
|---|---|---|---|---|---|---|
| AAATTGTAAA | CGTTAATATT | TTGTTAAAAT | TCGCGTTAAA | TTTTGTTAA | ATCAGCTCAT | 60 |
| TTTTTAACCA | ATAGGCCGAA | ATCGGCAAAA | TCCCTTATAA | ATCAAAAGAA | TAGACCGAGA | 120 |
| TAGGGTTGAG | TGTTGTTCCA | GTTTGGAACA | AGAGTCCACT | ATTAAAGAAC | GTGGACTCCA | 180 |
| ACGTCAAAGG | GCGAAAAACC | GTCTATCAGG | GCGATGGCCC | ACTACGTGAA | CCATCACCCT | 240 |
| AATCAAGTTT | TTTGGGGTCG | AGGTGCCGTA | AAGCACTAAA | TCGGAACCCT | AAAGGGAGCC | 300 |
| CCCGATTTAG | AGCTTGACGG | GGAAAGCCGG | CGAACGTGGC | GAGAAAGGAA | GGGAAGAAAG | 360 |
| CGAAAGGAGC | GGGCGCTAGG | GCGCTGGCAA | GTGTAGCGGT | CACGCTGCGC | GTAACCACCA | 420 |
| CACCCGCCGC | GCTTAATGCG | CCGCTACAGG | GCGCGTCCCA | TTCGCCATTC | AGGCTACGCA | 480 |

```
ACTGTTGGGA  AGGGCGATCG  GTGCGGGCCT  CTTCGCTATT  ACGCCAGCTG  GCGAAGGGGG   540
GATGTGCTGC  AAGGCGATTA  AGTTGGGTAA  CGCCAGGGTT  TTCCCAGTCA  CGACGTTGTA   600
AAACGACGGC  CAGTGAATTG  TAATACGACT  CACTATAGGG  CGAATTGAGC  TCCACCGCGG   660
TGGCGGCCGC  TCTAGCGATG  GCAGCCACCA  TTCATTTCTC  GATGCGACGG  TAAACGACGC   720
CCGCGGCAGA  TTAGGTCATT  GCCGAACGGA  TTGAAGCTCT  CTCCATCTTG  GATCCATTCC   780
CGGCCAATCC  CGTCTCGGCC  AACCACACTG  TCCACTCGCC  CAGGTCAGCA  GCTCAGGACT   840
CTCTCCTGGT  TTGGTACCGC  TTAGTGTAGA  GCATACCGCT  CTCAGTCCCC  ATAGACCAAC   900
CATAACACCG  CACGTTCTCT  TTCACTCAAG  ATGCTTATCA  TGTCCCTCT   TTCTGCTCCA   960
ATGATTCGGA  CTGGTCGAAT  ACCAATGAGA  CAAGCGAGAG  CGCAGTGCGA  GCAAGCGTTC  1020
CTGCAGATAG  AGCAGTGGGA  CTGCCGCGCC  ACAAAGGAAG  AGGATCGTGA  CGTGACGTGA  1080
CCAGTGACCA  GAAAGCAGAA  GATCCAAAAG  AGTCAAAAGG  ACCGAGCCTC  ACCTACAGTA  1140
ATGGCCCGGA  TGGCACTCAA  GACCGTCCTC  TCGGCCCTTT  CTCCAACTCT  TCTCCTTCCA  1200
TAATTCACCT  AGGTACATAC  ACGGCCTACG  CTTCCGCCTC  ATCCATCCC   ATCCATCCC   1260
ATCCATCCC   ATCGACGACT  CTAACCCGCC  CGCGAGTGCA  AACCTCGTCC  ACGAACGGAC  1320
ACCCCGGCTC  TCCTCCGAAG  CCCTTGCAAG  TGGAAGCTGA  GGTTGCCGAA  CTTAGACGAC  1380
CAGGTTCACC  AGCCGGACCG  CAACTCGAAC  GTCAGAATAC  AGCCTCAGCC  TCCAAAGGGG  1440
GTTAACGCCA  AGCGAGAGCA  AGACAAGATC  GTCGCCCATC  AATATCCTGG  ACAAGACAAC  1500
ATGGACGCAA  TATATAACCT  CAAGCAAGTC  CTCCTCAGCA  ACCATGATTT  CACCACCAGC  1560
CTGGTCTCCA  ACGCAACAGA  CTTCTCGACA  AGTCCCTTGA  CCTACTTCGC  CATGCATCTC  1620
GTCTCTTCGC  TCCTCGTCGT  GGGCGCCGCC  TTCCAGGCCG  TGCTCGGTCT  GCCGGATCCT  1680
CTGCATGAAA  AGAGGCACAG  CGACATCATC  AAGCGGTCTG  TCGACTCGTA  TATCCAGACC  1740
GAGACTCCCA  TTGCGCAGAA  GAACCTTCTG  TGCAACATCG  GTGCTTCTGG  ATGCAGAGCC  1800
TCCGGTGCTG  CCTCTGGTGT  TGTGGTTGCC  TCCCCTTCCA  AGTCGAGCCC  TGACTGTAAG  1860
TGGAAATTGC  ACAGTGTGTC  TCATCTCTCA  TGGCAGCATA  GCTCACAGTG  TCGATAGACT  1920
GGTATACCTG  GACTCGTGAT  GCCGCCCTTG  TCACCAAGCT  TATTGTCGAC  GAATTCCGGC  1980
GCGCCCCGG   GTTAATTAAG  TCTAGAGTGG  AGGTAAATCG  CTTGCTTCGT  ACTAGGTAGT  2040
AAGTAGTGAT  TGGGAAAAGG  AAATGAGAGA  ACGGGAACGG  GAACGGGAAC  GGGAATTTGT  2100
GATTACAAAG  TGTAAAATTA  ATAGGCCCGG  GATTTTGGTT  AGATGCATAA  GGGGGGCAGG  2160
GGGGGCTAGG  AAACGGAAGG  TTGCATATCA  ACCGAGGAAG  AATGGGAAGA  AAGGGAAGAA  2220
AGACAGAAAG  AAGGAACAAC  AGGACTTCAT  TCTCTCACAT  CGACATGAGC  TACCTGGGCA  2280
TCAGCTACCT  GGGCATCTTG  ATTTCCTTTT  TAGAAGATTG  TTTTGTATCC  TTTTTTCTTC  2340
CTCCCTTTTC  TTTTCTTGTC  CGTCTCTTAC  ACCTACCTAT  TTTTAGCCAA  AGTCCACACA  2400
CACACAAACT  TTTTGTTAGA  TATTCTCTGT  ATCAAAATTG  ACAAGTTTCA  ATGTTATACA  2460
GTACCTTGCC  AAGTTTAATA  CACATTCAAA  TCAATCAACC  ACACACACAC  AAGTTTTATT  2520
GTGCAGAAAT  GGAGTGAAGA  AGAAACATGT  TTGGGATTAT  GATGACAAGC  TTCTCAACAA  2580
AATTTCAACG  AGTTAAGCTT  CAAAGGTCCG  CTGGCTCAAT  GGCAGAGCGT  CTGACTACGA  2640
ATCAGGAGGT  TCCAGGTTCG  ACCCCTGGGT  GGATCGAGTT  GCAAATTGGT  ACTTTGAGTA  2700
CCAAAGTTCC  TTTTTTTTTT  TCGTTTGGCT  CTCTGCTTTT  CGACAGTTCA  CTGAGTCATG  2760
TGCAAGACAC  CCCTGATCGG  GTACGTACTG  AACTGCTTTT  GGTGCAGTGC  AATGGTTCTC  2820
GAGGGGGGGC  CCGGTACCCA  GCTTTTGTTC  CCTTTAGTGA  GGGTTAATTC  CGAGCTTGGC  2880
```

-continued

| | | | | | |
|---|---|---|---|---|---|
|GTAATCATGG|TCATAGCTGT|TTCCTGTGTG|AAATTGTTAT|CCGCTCACAA|TTCCACACAA|2940|
|CATAGGAGCC|GGAAGCATAA|AGTGTAAAGC|CTGGGGTGCC|TAATGAGTGA|GGTAACTCAC|3000|
|ATTAATTGCG|TTGCGCTCAC|TGCCCGCTTT|CCAGTCGGGA|AACCTGTCGT|GCCAGCTGCA|3060|
|TTAATGAATC|GGCCAACGCG|CGGGGAGAGG|CGGTTTGCGT|ATTGGGCGCT|CTTCCGCTTC|3120|
|CTCGCTCACT|GACTCGCTGC|GCTCGGTCGT|TCGGCTGCGG|CGAGCGGTAT|CAGCTCACTC|3180|
|AAAGGCGGTA|ATACGGTTAT|CCACAGAATC|AGGGGATAAC|GCAGGAAAGA|ACATGTGAGC|3240|
|AAAAGGCCAG|CAAAAGGCCA|GGAACCGTAA|AAAGGCCGCG|TTGCTGGCGT|TTTTCCATAG|3300|
|GCTCGGCCCC|CCTGACGAGC|ATCACAAAAA|TCGACGCTCA|AGTCAGAGGT|GGCGAAACCC|3360|
|GACAGGACTA|TAAAGATACC|AGGCGTTCCC|CCTGGAAGC|TCCCTCGTGC|GCTCTCCTGT|3420|
|TCCGACCCTG|CCGCTTACCG|GATACCTGTC|CGCCTTTCTC|CCTTCGGGAA|GCGTGGCGCT|3480|
|TTCTCAATGC|TCACGCTGTA|GGTATCTCAG|TTCGGTGTAG|GTCGTTCGCT|CCAAGCTGGG|3540|
|CTGTGTGCAC|GAACCCCCCG|TTCAGCCCGA|CCGCTGCGCC|TTATCCGGTA|ACTATCGTCT|3600|
|TGAGTCCAAC|CCGGTAAGAC|ACGACTTATC|GCCACTGGCA|GCAGCCACTG|GTAACAGGAT|3660|
|TAGCAGAGCG|AGGTATGTAG|GCGGTGCTAC|AGAGTTCTTG|AAGTGGTGGC|CTAACTACGG|3720|
|CTACACTAGA|AGGACAGTAT|TTGGTATCTG|CGCTCTGCTG|AAGCCAGTTA|CCTTCGGAAA|3780|
|AAGAGTTGGT|AGCTCTTGAT|CCGGCAAACA|AACCACCGCT|GGTAGCGGTG|GTTTTTTTGT|3840|
|TTGCAAGCAG|CAGATTACGC|GCAGAAAAAA|AGGATCTCAA|GAAGATCCTT|TGATCTTTTC|3900|
|TACGGGGTCT|GACGCTCAGT|GGAACGAAAA|CTCACGTTAA|GGGATTTTGG|TCATGAGATT|3960|
|ATCAAAAGG|ATCTTCACCT|AGATCCTTTT|AAATTAAAAA|TGAAGTTTTA|AATCAATCTA|4020|
|AAGTATATAT|GAGTAAACTT|GGTCTGACAG|TTACCAATGC|TTAATCAGTG|AGGCACCTAT|4080|
|CTCAGCGATC|TGTCTATTTC|GTTCATCCAT|AGTTGCCTGA|CTGCCCGTCG|TGTAGATAAC|4140|
|TACGATACGG|GAGGGCTTAC|CATCTGGCCC|CAGTGCTGCA|ATGATACCGC|GAGACCCACG|4200|
|CTCACCGGCT|CCAGATTTAT|CAGCAATAAA|CCAGCCAGCC|GGAAGGGCCG|AGCGCAGAAG|4260|
|TGGTCCTGCA|ACTTTATCCG|CCTCCATCCA|GTCTATTAAT|TGTTGCCGGG|AAGCTAGAGT|4320|
|AAGTAGTTCG|CCAGTTAATA|GTTTGCGCAA|CGTTGTTGCC|ATTGCTACAG|GCATCGTGGT|4380|
|GTCACGCTCG|TCGTTTGGTA|TGGCTTCATT|CAGCTCCGGT|TCCCAACGAT|CAAGGCGAGT|4440|
|TACATGATCC|CCCATGTTGT|GAAAAAAGC|GGTTAGCTCC|TTCGGTCCTC|CGATCGTTGT|4500|
|CAGAAGTAAG|TTGGCCGCAG|TGTTATCACT|CATGCTTATG|GCAGCACTGC|ATAATTCTCT|4560|
|TACTGTCATG|CCATCCGTAA|GATGCTTTTC|TGTGACTGGT|GAGTACTCAA|CCAAGTCATT|4620|
|CTGAGAATAG|TGTATGCGGC|GACCGAGTTG|CTCTTGCCCG|GCGTCAATAC|GGGATAATAC|4680|
|CGCGCCACAT|AGCAGAACTT|TAAAAGTGCT|CATCATTGGA|AAACGTTCTT|CGGGGCGAAA|4740|
|ACTCTCAAGG|ATCTTACCGC|TGTTGAGATC|CAGTTCGATG|TAACCCACTC|GTGCACCCAA|4800|
|CTGATCTTCA|GCATCTTTTA|CTTTCACCAG|CGTTTCTGGG|TGAGCAAAAA|CAGGAAGGCA|4860|
|AAATGCCGCA|AAAAAGGGAA|TAAGGGCGAC|ACGGAAATGT|TGAATACTCA|TACTCTTCCT|4920|
|TTTTCAATAT|TATTGAAGCA|TTTATCAGGG|TTATTGTCTC|ATGAGCGGAT|ACATATTTGA|4980|
|ATGTATTTAG|AAAAATAAAC|AAATAGGGGT|TCCGCGCACA|TTTCCCCGAA|AAGTGCCACC|5040|
|TG|||||| 5042|

( 2 ) INFORMATION FOR SEQ ID NO: 2:

( i ) SEQUENCE CHARACTERISTICS:
        ( A ) LENGTH: 4792 base pairs
        ( B ) TYPE: nucleic acid -continued ( C ) STRANDEDNESS: double
( D ) TOPOLOGY: circular ( i i ) MOLECULE TYPE: other nucleic acid
( A ) DESCRIPTION: /desc = "Plasmid pGS"

( x i ) SEQUENCE DESCRIPTION: SEQ ID NO: 2:

```
AAATTGTAAA CGTTAATATT TTGTTAAAAT TCGCGTTAAA TTTTTGTTAA ATCAGCTCAT      60
TTTTTAACCA ATAGGCCGAA ATCGGCAAAA TCCCTTATAA ATCAAAAGAA TAGACCGAGA     120
TAGGGTTGAG TGTTGTTCCA GTTTGGAACA AGAGTCCACT ATTAAAGAAC GTGGACTCCA     180
ACGTCAAAGG GCGAAAAACC GTCTATCAGG GCGATGGCCC ACTACGTGAA CCATCACCCT     240
AATCAAGTTT TTTGGGGTCG AGGTGCCGTA AAGCACTAAA TCGGAACCCT AAAGGGAGCC     300
CCCGATTTAG AGCTTGACGG GGAAAGCCGG CGAACGTGGC GAGAAAGGAA GGGAAGAAAG     360
CGAAAGGAGC GGGCGCTAGG GCGCTGGCAA GTGTAGCGGT CACGCTGCGC GTAACCACCA     420
CACCCGCCGC GCTTAATGCG CCGCTACAGG GCGCGTCCCA TTCGCCATTC AGGCTACGCA     480
ACTGTTGGGA AGGGCGATCG GTGCGGGCCT CTTCGCTATT ACGCCAGCTG GCGAAGGGGG     540
GATGTGCTGC AAGGCGATTA AGTTGGGTAA CGCCAGGGTT TTCCCAGTCA CGACGTTGTA     600
AAACGACGGC CAGTGAATTG TAATACGACT CACTATAGGG CGAATTGAGC TCCACCGCGG     660
TGGCGGCCGC TCTAGCGATG GCAGCCACCA TTCATTTCTC GATGCGACGG TAAACGACGC     720
CCGCGGCAGA TTAGGTCATT GCCGAACGGA TTGAAGCTCT CTCCATCTTG GATCCATTCC     780
CGGCCAATCC CGTCTCGGCC AACCACACTG TCCACTCGCC CAGGTCAGCA GCTCAGGACT     840
CTCTCCTGGT TTGGTACCGC TTAGTGTAGA GCATACCGCT CTCAGTCCCC ATAGACCAAC     900
CATAACACCG CACGTTCTCT TTCACTCAAG ATGCTTATCA TGTCCCCTCT TTCTGCTCCA     960
ATGATTCGGA CTGGTCGAAT ACCAATGAGA CAAGCGAGAG CGCAGTGCGA GCAAGCGTTC    1020
CTGCAGATAG AGCAGTGGGA CTGCCGCGCC ACAAGGAAG AGGATCGTGA CGTGACGTGA    1080
CCAGTGACCA GAAAGCAGAA GATCCAAAAG AGTCAAAAGG ACCGAGCCTC ACCTACAGTA    1140
ATGGCCCGGA TGGCACTCAA GACCGTCCTC TCGGCCCTTT CTCCAACTCT TCTCCTTCCA    1200
TAATTCACCT AGGTACATAC ACGGCCTACG CTTCCGCCTC ATCCATCCC ATCCATCCC      1260
ATCCATCCC ATCGACGACT CTAACCCGCC CGCGAGTGCA AACCTCGTCC ACGAACGGAC    1320
ACCCCGGCTC TCCTCCGAAG CCCTTGCAAG TGGAAGCTGA GGTTGCCGAA CTTAGACGAC    1380
CAGGTTCACC AGCCGGACCG CAACTCGAAC GTCAGAATAC AGCCTCAGCC TCCAAAGGGG    1440
GTTAACGCCA AGCGAGAGCA AGACAAGATC GTCGCCCATC AATATCCTGG ACAAGACAAC    1500
ATGGACGCAA TATATAACCT CAAGCAAGTC CTCCTCAGCA ACCATGATTT CACCACCAGC    1560
CTGGTCTCCA ACGCAACAGA CTTCTCGACA AGTCCCTTGA CCTACTTCGC CATGCATCTC    1620
GTCTCTTCGC TCCTCGTCGT GGGCGCCGCC TTCCAGGCCG TGCTCGGTCT GCCGGATCCT    1680
CTGCATGAAA AGAGGCACAG CGACATCATC AAGCGGTCTG TCGACCGGAC GCGCCCCGG     1740
GTTAATTAAG TCTAGAGTGG AGGTAAATCG CTTGCTTCGT ACTAGGTAGT AAGTAGTGAT    1800
TGGGAAAAGG AAATGAGAGA ACGGGAACGG GAACGGGAAC GGGAATTTGT GATTACAAAG    1860
TGTAAAATTA ATAGGCCCGG GATTTTGGTT AGATGCATAA GGGGGGCAGG GGGGGCTAGG    1920
AAACGGAAGG TTGCATATCA ACCGAGGAAG AATGGGAAGA AAGGGAAGAA AGACAGAAAG    1980
AAGGAACAAC AGGACTTCAT TCTCTCACAT CGACATGAGC TACCTGGGCA TCAGCTACCT    2040
GGGCATCTTG ATTTCCTTTT TAGAAGATTG TTTTGTATCC TTTTTCTTC CTCCCTTTTC     2100
TTTTCTTGTC CGTCTCTTAC ACCTACCTAT TTTAGCCAA AGTCCACACA CACACAAACT     2160
```

-continued

| | | | | | | |
|---|---|---|---|---|---|---|
| TTTTGTTAGA | TATTCTCTGT | ATCAAAATTG | ACAAGTTTCA | ATGTTATACA | GTACCTTGCC | 2220 |
| AAGTTTAATA | CACATTCAAA | TCAATCAACC | ACACACACAC | AAGTTTTATT | GTGCAGAAAT | 2280 |
| GGAGTGAAGA | AGAAACATGT | TTGGGATTAT | GATGACAAGC | TTCTCAACAA | AATTTCAACG | 2340 |
| AGTTAAGCTT | CAAAGGTCCG | CTGGCTCAAT | GGCAGAGCGT | CTGACTACGA | ATCAGGAGGT | 2400 |
| TCCAGGTTCG | ACCCCTGGGT | GGATCGAGTT | GCAAATTGGT | ACTTTGAGTA | CCAAAGTTCC | 2460 |
| TTTTTTTTTT | TCGTTTGGCT | CTCTGCTTTT | CGACAGTTCA | CTGAGTCATG | TGCAAGACAC | 2520 |
| CCCTGATCGG | GTACGTACTG | AACTGCTTTT | GGTGCAGTGC | AATGGTTCTC | GAGGGGGGGC | 2580 |
| CCGGTACCCA | GCTTTTGTTC | CCTTTAGTGA | GGGTTAATTC | CGAGCTTGGC | GTAATCATGG | 2640 |
| TCATAGCTGT | TTCCTGTGTG | AAATTGTTAT | CCGCTCACAA | TTCCACACAA | CATAGGAGCC | 2700 |
| GGAAGCATAA | AGTGTAAAGC | CTGGGGTGCC | TAATGAGTGA | GGTAACTCAC | ATTAATTGCG | 2760 |
| TTGCGCTCAC | TGCCCGCTTT | CCAGTCGGGA | AACCTGTCGT | GCCAGCTGCA | TTAATGAATC | 2820 |
| GGCCAACGCG | CGGGGAGAGG | CGGTTTGCGT | ATTGGGCGCT | CTTCCGCTTC | CTCGCTCACT | 2880 |
| GACTCGCTGC | GCTCGGTCGT | TCGGCTGCGG | CGAGCGGTAT | CAGCTCACTC | AAAGGCGGTA | 2940 |
| ATACGGTTAT | CCACAGAATC | AGGGGATAAC | GCAGGAAAGA | ACATGTGAGC | AAAAGGCCAG | 3000 |
| CAAAAGGCCA | GGAACCGTAA | AAAGGCCGCG | TTGCTGGCGT | TTTTCCATAG | GCTCGGCCCC | 3060 |
| CCTGACGAGC | ATCACAAAAA | TCGACGCTCA | AGTCAGAGGT | GGCGAAACCC | GACAGGACTA | 3120 |
| TAAAGATACC | AGGCGTTCCC | CCCTGGAAGC | TCCCTCGTGC | GCTCTCCTGT | TCCGACCCTG | 3180 |
| CCGCTTACCG | GATACCTGTC | CGCCTTTCTC | CCTTCGGGAA | GCGTGGCGCT | TTCTCAATGC | 3240 |
| TCACGCTGTA | GGTATCTCAG | TTCGGTGTAG | GTCGTTCGCT | CCAAGCTGGG | CTGTGTGCAC | 3300 |
| GAACCCCCCG | TTCAGCCCGA | CCGCTGCGCC | TTATCCGGTA | ACTATCGTCT | TGAGTCCAAC | 3360 |
| CCGGTAAGAC | ACGACTTATC | GCCACTGGCA | GCAGCCACTG | GTAACAGGAT | TAGCAGAGCG | 3420 |
| AGGTATGTAG | GCGGTGCTAC | AGAGTTCTTG | AAGTGGTGGC | CTAACTACGG | CTACACTAGA | 3480 |
| AGGACAGTAT | TTGGTATCTG | CGCTCTGCTG | AAGCCAGTTA | CCTTCGGAAA | AAGAGTTGGT | 3540 |
| AGCTCTTGAT | CCGGCAAACA | AACCACCGCT | GGTAGCGGTG | GTTTTTTTGT | TTGCAAGCAG | 3600 |
| CAGATTACGC | GCAGAAAAAA | AGGATCTCAA | GAAGATCCTT | TGATCTTTTC | TACGGGGTCT | 3660 |
| GACGCTCAGT | GGAACGAAAA | CTCACGTTAA | GGGATTTTGG | TCATGAGATT | ATCAAAAAGG | 3720 |
| ATCTTCACCT | AGATCCTTTT | AAATTAAAAA | TGAAGTTTTA | AATCAATCTA | AAGTATATAT | 3780 |
| GAGTAAACTT | GGTCTGACAG | TTACCAATGC | TTAATCAGTG | AGGCACCTAT | CTCAGCGATC | 3840 |
| TGTCTATTTC | GTTCATCCAT | AGTTGCCTGA | CTGCCCGTCG | TGTAGATAAC | TACGATACGG | 3900 |
| GAGGGCTTAC | CATCTGGCCC | CAGTGCTGCA | ATGATACCGC | GAGACCCACG | CTCACCGGCT | 3960 |
| CCAGATTTAT | CAGCAATAAA | CCAGCCAGCC | GGAAGGGCCG | AGCGCAGAAG | TGGTCCTGCA | 4020 |
| ACTTTATCCG | CCTCCATCCA | GTCTATTAAT | TGTTGCCGGG | AAGCTAGAGT | AAGTAGTTCG | 4080 |
| CCAGTTAATA | GTTTGCGCAA | CGTTGTTGCC | ATTGCTACAG | GCATCGTGGT | GTCACGCTCG | 4140 |
| TCGTTTGGTA | TGGCTTCATT | CAGCTCCGGT | TCCCAACGAT | CAAGGCGAGT | TACATGATCC | 4200 |
| CCCATGTTGT | GAAAAAAAGC | GGTTAGCTCC | TTCGGTCCTC | CGATCGTTGT | CAGAAGTAAG | 4260 |
| TTGGCCGCAG | TGTTATCACT | CATGCTTATG | GCAGCACTGC | ATAATTCTCT | TACTGTCATG | 4320 |
| CCATCCGTAA | GATGCTTTTC | TGTGACTGGT | GAGTACTCAA | CCAAGTCATT | CTGAGAATAG | 4380 |
| TGTATGCGGC | GACCGAGTTG | CTCTTGCCCG | GCGTCAATAC | GGGATAATAC | CGCGCCACAT | 4440 |
| AGCAGAACTT | TAAAAGTGCT | CATCATTGGA | AAACGTTCTT | CGGGGCGAAA | ACTCTCAAGG | 4500 |
| ATCTTACCGC | TGTTGAGATC | CAGTTCGATG | TAACCCACTC | GTGCACCCAA | CTGATCTTCA | 4560 |

| | | | | | |
|---|---|---|---|---|---|
| GCATCTTTTA | CTTTCACCAG | CGTTTCTGGG | TGAGCAAAAA | CAGGAAGGCA | AAATGCCGCA | 4620 |
| AAAAGGGAA | TAAGGGCGAC | ACGGAAATGT | TGAATACTCA | TACTCTTCCT | TTTTCAATAT | 4680 |
| TATTGAAGCA | TTTATCAGGG | TTATTGTCTC | ATGAGCGGAT | ACATATTTGA | ATGTATTTAG | 4740 |
| AAAAATAAAC | AAATAGGGGT | TCCGCGCACA | TTTCCCCGAA | AAGTGCCACC | TG | 4792 |

( 2 ) INFORMATION FOR SEQ ID NO: 3:

( i ) SEQUENCE CHARACTERISTICS:
        ( A ) LENGTH: 3796 base pairs
        ( B ) TYPE: nucleic acid
        ( C ) STRANDEDNESS: double
        ( D ) TOPOLOGY: circular ( i i ) MOLECULE TYPE: other nucleic acid
        ( A ) DESCRIPTION: /desc = "Plasmid pgla Xho-"

( x i ) SEQUENCE DESCRIPTION: SEQ ID NO: 3:

| | | | | | |
|---|---|---|---|---|---|
| AAAAGCTGGA | ATTCGAGCTC | CACCGCGGTG | GCGGCCGCTC | TAGAACTAGT | GGATCCCCCG | 60 |
| GGCTGCAGGA | ATTCGATATC | AAGCTTATCG | ATGGCAGCCA | CCATTCATTT | CTCGATGCGA | 120 |
| CGGTAAACGA | CGCCCGCGGC | AGATTAGGTC | ATTGCCGAAC | GGATTGAAGC | TCTCTCCATC | 180 |
| TTGGATCCAT | TCCCGGCCAA | TCCCGTCTCG | GCCAACCACA | CTGTCCACTC | GCCCAGGTCA | 240 |
| GCAGCTCAGG | ACTCTCTCCT | GGTTTGGTAC | CGCTTAGTGT | AGAGCATACC | GCTCTCAGTC | 300 |
| CCCATAGACC | AACCATAACA | CCGCACGTTC | TCTTTCACTC | AAGATGCTTA | TCATGTCCCC | 360 |
| TCTTTCTGCT | CCAATGATTC | GGACTGGTCG | AATACCAATG | AGACAAGCGA | GAGCGCAGTG | 420 |
| CGAGCAAGCG | TTCCTGCAGA | TAGAGCAGTG | GGACTGCCGC | GCCACAAAGG | AAGAGGATCG | 480 |
| TGACGTGACG | TGACCAGTGA | CCAGAAAGCA | GAAGATCCAA | AAGAGTCAAA | AGGACCGAGC | 540 |
| CTCACCTACA | GTAATGGCCC | GGATGGCACT | CAAGACCGTC | CTCTCGGCCC | TTTCTCCAAC | 600 |
| TCTTCTCCTT | CCATAATTCA | CCTAGGTACA | TACACGGCCT | ACGCTTCCGC | CTCATCCCAT | 660 |
| CCCATCCCAT | CCCATCCCAT | CCCATCGACG | ACTCTAACCC | GCCCGCGAGT | GCAAACCTCG | 720 |
| TCCACGAACG | GACACCCCGG | CTCTCCTCCG | AAGCCCTTGC | AAGTGGAAGC | TGAGGTTGCC | 780 |
| GAACTTAGAC | GACCAGGTTC | ACCAGCCGGA | CCGCAACTCG | AACGTCAGAA | TACAGCCTCA | 840 |
| GCCTCCAAAG | GGGGTTAACG | CCAAGCGAGA | GCAAGACAAG | ATCGTCGCCC | ATCAATATCC | 900 |
| TGGACAAGAC | AACATGGACG | CAATATATAA | CCTCAAGCAA | GTCCTCCTCA | GCAACCATGA | 960 |
| TTTCACCACC | AGCCTGGTCT | CCAACGCAAC | AGACTTCTCG | ACAAGTCCCT | TGACCTACTT | 1020 |
| CGCCATGCAT | CTCGTCTCTT | CGCTCCTCGT | CGTGGGCGCC | GCCTTCCAGG | CCGTGCTCGG | 1080 |
| TCTGCCGGAT | CCTCTGCATG | AAAAGAGGCA | CAGCGACATC | ATCAAGCGGT | CTGTCGACTC | 1140 |
| GTATATCCAG | ACCGAGACTC | CCATTGCGCA | GAAGAACCTT | CTGTGCAACA | TCGGTGCTTC | 1200 |
| TGGATGCAGA | GCCTCCGGTG | CTGCCTCTGG | TGTTGTGGTT | GCCTCCCCTT | CCAAGTCGAG | 1260 |
| CCCTGACTGT | AAGTGGAAAT | TGCACAGTGT | GTCTCATCTC | TCATGGCAGC | ATAGCTCACA | 1320 |
| GTGTCGATAG | ACTGGTATAC | CTGGACTCGT | GATGCCGCCC | TTGTCACCAA | GCTTATTGTC | 1380 |
| GACGAATTCA | CCAACGACTA | CAACACCACT | CTTCAGAACA | CCATTCAGGC | TTATGCTGCT | 1440 |
| GCACAGGCCA | AGCTTCAGGG | CGTTAGCAAC | CCGTCCGGTT | CCCTCTCCAA | CGGGGCCGGT | 1500 |
| CTTGGTGAGC | CCAAGTTCAT | GGTCGACCTC | CAGCAGTTCA | CCGGTGCCTG | GGGCCGCCCC | 1560 |
| CAGAGGGATG | GCCCTCCCCT | TCGCGCCATT | GCCCTGATCG | GCTATGGCAA | GTGGCTCGTC | 1620 |
| AGCAACGGTT | ATGCTGATAC | GGCCAAGAGC | ATCATCTGGC | CCATTGTGAA | GAACGACCTT | 1680 |
| GCCTACACTG | CCCAGTACTG | GAACAACACT | GGCTTCGATC | TCTGGGAGGA | GGTTAACAGC | 1740 |

-continued

```
TCTTCTTTCT TCACCATCGC CGCCTCCCAC CGTGCTCTCG TTGAGGGTTC TGCTTTTGCC     1800
AAGTCCGTCG GCAGCTCTTG CAGCGCTTGC GATGCCATTG CCCCCCAAAT TCTGTGCTTC     1860
CAGCAGAGCT TCTGGTCCAA CAGCGGCTAC ATCATCTCCA ACTTTGTCAA CTACCGCAGC     1920
GGCAAGGACA TCAACTCCGT CTTGACTTCC ATCCACAACT TCGACCCCGC TGCCGGTTGC     1980
GATGTCAACA CCTTCCAGCC CTGCAGCGAC CGGGCTCTTG CCAACCACAA GGTTGTCGTT     2040
GACTCCATGC GCTTCTGGGG TGTCAACTCC GGTCGCACTG CCGGTAAGGC CGCCGCTGTC     2100
GGTCGCTACG CTGAGGATGT CTACTACAAC GGTAACCCGT GGTACCTCGC TACTCTCGCC     2160
GCCGCCGAGC AGCTCTACGA CGCCGTCTAC GTCTGGAAGA AGCAGGGTTC TATCACTGTC     2220
ACCTCCACCT CCCTCGCCTT CTTCAAGGAC CTCGTTCCCT CCGTCAGCAC CGGCACCTAC     2280
TCCAGCTCTT CCTCCACCTA CACCGCCATC ATCAACGCCG TCACCACCTA TGCCGACGGC     2340
TTCGTCGACA TCGTTGCCCA GTACACTCCC TCCGACGGCT CCCTGGCCGA GCAGTTCGAC     2400
AAGGATTCGG GCGCCCCCCT CAGCGCCACC CACCTGACCT GGTCGTACGC CTCCTTCCTT     2460
TCCGCCGCCG CCCGCCGCGC CGGCATCGTC CCTCCCTCGT GGGGCGCCGC GTCCGCCAAC     2520
TCTCTGCCCG GTTCCTGCTC CGCCTCCACC GTCGCCGGTT CATACGCCAC CGCGACTGCC     2580
ACCTCCTTTC CCGCCAACCT CACGCCCGCC AGCACCACCG TCACCCCTCC CACGCAGACC     2640
GGCTGCGCCG CCGACCACGA GGTTTTGGTA ACTTTCAACG AAAAGGTCAC CACCAGCTAT     2700
GGTCAGACGG TCAAGGTCGT CGGCAGCATC GCTCGGCTCG GCAACTGGGC CCCCGCCAGC     2760
GGGCTCACCC TGTCGGCCAA ACAGTACTCT TCCAGCAACC CGCTCTGGTC CACCACTATT     2820
GCGCTGCCCC AGGGCACCTC GTTCAAGTAC AAGTATGTCG TCGTCAACTC GGATGGGTCC     2880
GTCAAGTGGG AGAACGATCC TGACCGCAGC TATGCTGTTG GGACGGACTG CGCCTCTACT     2940
GCGACTCTTG ATGATACGTG GAGGTAAATC GCTTGCTTCG TACTAGGTAG TAAGTAGTGA     3000
TTGGGAAAAG GAAATGAGAG AACGGGAACG GGAACGGGAA CGGGAATTTG TGATTACAAA     3060
GTGTAAAATT AATAGGCCCG GGATTTTGGT TAGATGCATA AGGGGGGCAG GGGGGGCTAG     3120
GAAACGGAAG GTTGCATATC AACCGAGGAA GAATGGGAAG AAAGGGAAGA AAGACAGAAA     3180
GAAGGAACAA CAGGACTTCA TTCTCTCACA TCGACATGAG CTACCTGGGC ATCAGCTACC     3240
TGGGCATCTT GATTTCCTTT TTAGAAGATT GTTTTGTATC CTTTTTTCTT CCTCCCTTTT     3300
CTTTTCTTGT CCGTCTCTTA CACCTACCTA TTTTTAGCCA AAGTCCACAC ACACACAAAC     3360
TTTTTGTTAG ATATTCTCTG TATCAAAATT GACAAGTTTC AATGTTATAC AGTACCTTGC     3420
CAAGTTTAAT ACACATTCAA ATCAATCAAC CACACACACA CAAGTTTTAT TGTGCAGAAA     3480
TGGAGTGAAG AAGAAACATG TTTGGGATTA TGATGACAAG CTTCTCAACA AAATTTCAAC     3540
GAGTTAAGCT TCAAAGGTCC GCTGGCTCAA TGGCAGAGCG TCTGACTACG AATCAGGAGG     3600
TTCCAGGTTC GACCCCTGGG TGGATCGAGT TGCAAATTGG TACTTTGAGT ACCAAAGTTC     3660
CTTTTTTTTT TTCGTTTGGC TCTCTGCTTT TCGACAGTTC ACTGAGTCAT GTGCAAGACA     3720
CCCCTGATCG GGTACGTACT GAACTGCTTT TGGTGCAGTG CAATGGTTCT CGAGGGGGGG     3780
CCCGGTACCC AATTCG                                                    3796
```

( 2 ) INFORMATION FOR SEQ ID NO: 4:

( i ) SEQUENCE CHARACTERISTICS:
        ( A ) LENGTH: 1881 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 4:

| | | | | | |
|---|---|---|---|---|---|
| ATGCATCTCG | TCTCTTCGCT | CCTCGTCGTG | GGCGCCGCCT | TCCAGGCCGT | GCTCGGTCTG | 60 |
| CCGGATCCTC | TGCATGAAAA | GAGGCACAGC | GACATCATCA | AGCGGTCTGT | CGACTCGTAT | 120 |
| ATCCAGACCG | AGACTCCCAT | TGCGCAGAAG | AACCTTCTGT | GCAACATCGG | TGCTTCTGGA | 180 |
| TGCAGAGCCT | CCGGTGCTGC | CTCTGGTGTT | GTGGTTGCCT | CCCCTTCCAA | GTCGAGCCCT | 240 |
| GACTACTGGT | ATACCTGGAC | TCGTGATGCC | GCCCTTGTCA | CCAAGCTTAT | TGTCGACGAA | 300 |
| TTCACCAACG | ACTACAACAC | CACTCTTCAG | AACACCATTC | AGGCTTATGC | TGCTGCACAG | 360 |
| GCCAAGCTTC | AGGGCGTTAG | CAACCCGTCC | GGTTCCCTCT | CCAACGGGGC | CGGTCTTGGT | 420 |
| GAGCCCAAGT | TCATGGTCGA | CCTCCAGCAG | TTCACCGGTG | CCTGGGGCCG | CCCCCAGAGG | 480 |
| GATGGCCCTC | CCCTTCGCGC | CATTGCCCTG | ATCGGCTATG | GCAAGTGGCT | CGTCAGCAAC | 540 |
| GGTTATGCTG | ATACGGCCAA | GAGCATCATC | TGGCCCATTG | TGAAGAACGA | CCTTGCCTAC | 600 |
| ACTGCCCAGT | ACTGGAACAA | CACTGGCTTC | GATCTCTGGG | AGGAGGTTAA | CAGCTCTTCT | 660 |
| TTCTTCACCA | TCGCCGCCTC | CCACCGTGCT | CTCGTTGAGG | GTTCTGCTTT | TGCCAAGTCC | 720 |
| GTCGGCAGCT | CTTGCAGCGC | TTGCGATGCC | ATTGCCCCCC | AAATTCTGTG | CTTCCAGCAG | 780 |
| AGCTTCTGGT | CCAACAGCGG | CTACATCATC | TCCAACTTTG | TCAACTACCG | CAGCGGCAAG | 840 |
| GACATCAACT | CCGTCTTGAC | TTCCATCCAC | AACTTCGACC | CCGCTGCCGG | TTGCGATGTC | 900 |
| AACACCTTCC | AGCCCTGCAG | CGACCGGGCT | CTTGCCAACC | ACAAGGTTGT | CGTTGACTCC | 960 |
| ATGCGCTTCT | GGGGTGTCAA | CTCCGGTCGC | ACTGCCGGTA | AGGCCGCCGC | TGTCGGTCGC | 1020 |
| TACGCTGAGG | ATGTCTACTA | CAACGGTAAC | CCGTGGTACC | TCGCTACTCT | CGCCGCCGCC | 1080 |
| GAGCAGCTCT | ACGACGCCGT | CTACGTCTGG | AAGAAGCAGG | GTTCTATCAC | TGTCACCTCC | 1140 |
| ACCTCCCTCG | CCTTCTTCAA | GGACCTCGTT | CCCTCCGTCA | GCACCGGCAC | CTACTCCAGC | 1200 |
| TCTTCCTCCA | CCTACACCGC | CATCATCAAC | GCCGTCACCA | CCTATGCCGA | CGGCTTCGTC | 1260 |
| GACATCGTTG | CCCAGTACAC | TCCCTCCGAC | GGCTCCCTGG | CCGAGCAGTT | CGACAAGGAT | 1320 |
| TCGGGCGCCC | CCCTCAGCGC | CACCCACCTG | ACCTGGTCGT | ACGCCTCCTT | CCTTTCCGCC | 1380 |
| GCCGCCCGCC | GCGCCGGCAT | CGTCCCTCCC | TCGTGGGGCG | CCGCGTCCGC | CAACTCTCTG | 1440 |
| CCCGGTTCCT | GCTCCGCCTC | CACCGTCGCC | GGTTCATACG | CCACCGCGAC | TGCCACCTCC | 1500 |
| TTTCCCGCCA | ACCTCACGCC | CGCCAGCACC | ACCGTCACCC | CTCCCACGCA | GACCGGCTGC | 1560 |
| GCCGCCGACC | ACGAGGTTTT | GGTAACTTTC | AACGAAAAGG | TCACCACCAG | CTATGGTCAG | 1620 |
| ACGGTCAAGG | TCGTCGGCAG | CATCGCTCGG | CTCGGCAACT | GGGCCCCCGC | CAGCGGGCTC | 1680 |
| ACCCTGTCGG | CCAAACAGTA | CTCTTCCAGC | AACCCGCTCT | GGTCCACCAC | TATTGCGCTG | 1740 |
| CCCCAGGGCA | CCTCGTTCAA | GTACAAGTAT | GTCGTCGTCA | ACTCGGATGG | GTCCGTCAAG | 1800 |
| TGGGAGAACG | ATCCTGACCG | CAGCTATGCT | GTTGGGACGG | ACTGCGCCTC | TACTGCGACT | 1860 |
| CTTGATGATA | CGTGGAGGTA | A | | | | 1881 |

( 2 ) INFORMATION FOR SEQ ID NO: 5:

( i ) SEQUENCE CHARACTERISTICS:
        ( A ) LENGTH: 3041 base pairs
        ( B ) TYPE: nucleic acid
        ( C ) STRANDEDNESS: double
        ( D ) TOPOLOGY: circular ( i i ) MOLECULE TYPE: other nucleic acid
        ( A ) DESCRIPTION: /desc = "Plasmid pgla-mro"

( x i ) SEQUENCE DESCRIPTION: SEQ ID NO: 5:

| | | | | | | |
|---|---|---|---|---|---|---|
| AAAAGCTGGA | ATTCGAGCTC | CACCGCGGTG | GCGGCCGCTC | TAGAACTAGT | GGATCCCCCG | 60 |
| GGCTGCAGGA | ATTCGATATC | AAGCTTATCG | ATGGCAGCCA | CCATTCATTT | CTCGATGCGA | 120 |
| CGGTAAACGA | CGCCCGCGGC | AGATTAGGTC | ATTGCCGAAC | GGATTGAAGC | TCTCTCCATC | 180 |
| TTGGATCCAT | TCCCGGCCAA | TCCCGTCTCG | GCCAACCACA | CTGTCCACTC | GCCCAGGTCA | 240 |
| GCAGCTCAGG | ACTCTCTCCT | GGTTTGGTAC | CGCTTAGTGT | AGAGCATACC | GCTCTCAGTC | 300 |
| CCCATAGACC | AACCATAACA | CCGCACGTTC | TCTTTCACTC | AAGATGCTTA | TCATGTCCCC | 360 |
| TCTTTCTGCT | CCAATGATTC | GGACTGGTCG | AATACCAATG | AGACAAGCGA | GAGCGCAGTG | 420 |
| CGAGCAAGCG | TTCCTGCAGA | TAGAGCAGTG | GGACTGCCGC | GCCACAAAGG | AAGAGGATCG | 480 |
| TGACGTGACG | TGACCAGTGA | CCAGAAAGCA | GAAGATCCAA | AAGAGTCAAA | AGGACCGAGC | 540 |
| CTCACCTACA | GTAATGGCCC | GGATGGCACT | CAAGACCGTC | CTCTCGGCCC | TTTCTCCAAC | 600 |
| TCTTCTCCTT | CCATAATTCA | CCTAGGTACA | TACACGGCCT | ACGCTTCCGC | CTCATCCCAT | 660 |
| CCCATCCCAT | CCCATCCCAT | CCCATCGACG | ACTCTAACCC | GCCCGCGAGT | GCAAACCTCG | 720 |
| TCCACGAACG | GACACCCCGG | CTCTCCTCCG | AAGCCCTTGC | AAGTGGAAGC | TGAGGTTGCC | 780 |
| GAACTTAGAC | GACCAGGTTC | ACCAGCCGGA | CCGCAACTCG | AACGTCAGAA | TACAGCCTCA | 840 |
| GCCTCCAAAG | GGGGTTAACG | CCAAGCGAGA | GCAAGACAAG | ATCGTCGCCC | ATCAATATCC | 900 |
| TGGACAAGAC | AACATGGACG | CAATATATAA | CCTCAAGCAA | GTCCTCCTCA | GCAACCATGA | 960 |
| TTTCACCACC | AGCCTGGTCT | CCAACGCAAC | AGACTTCTCG | ACAAGTCCCT | TGACCTACTT | 1020 |
| CGCCATGCAT | CTCGTCTCTT | CGCTCCTCGT | CGTGGGCGCC | GCCTTCCAGG | CCGTGCTCGG | 1080 |
| TCTGCCGGAT | CCTCTGCATG | AAAAGAGGCA | CAGCGACATC | ATCAAGCGGT | CTGTCGACTC | 1140 |
| GTATATCCAG | ACCGAGACTC | CCATTGCGCA | GAAGAACCTT | CTGTGCAACA | TCGGTGCTTC | 1200 |
| TGGATGCAGA | GCCTCCGGTG | CTGCCTCTGG | TGTTGTGGTT | GCCTCCCCTT | CCAAGTCGAG | 1260 |
| CCCTGACTGT | AAGTGGAAAT | TGCACAGTGT | GTCTCATCTC | TCATGGCAGC | ATAGCTCACA | 1320 |
| GTGTCGATAG | ACTGGTATAC | CTGGACTCGT | GATGCCGCCC | TTGTCACCAA | GCTTATTGTC | 1380 |
| GACGAATTCA | CCAACGACTA | CAACACCACT | CTTCAGAACA | CCATTCAGGC | TTATGCTGCT | 1440 |
| GCACAGGCCA | AGCTTCAGGG | CGTTAGCAAC | CCGTCCGGTT | CCCTCTCCAA | CGGGGCCGGT | 1500 |
| CTTGGTGAGC | CCAAGTTCAT | GGTCGACCTC | CAGCAGTTCA | CCGGTGCCTG | GGGCCGCCCC | 1560 |
| CAGAGGGATG | GCCCTCCCCT | TCGCGCCATT | GCCCTGATCG | CTATGGCAA | GTGGCTCGTC | 1620 |
| AGCAACGGTT | ATGCTGATAC | GGCCAAGAGC | ATCATCTGGC | CCATTGTGAA | GAACGACCTT | 1680 |
| GCCTACACTG | CCCAGTACTG | GAACAACACT | GGCTTCGATC | TCTGGGAGGA | GGTTAACAGC | 1740 |
| TCTTCTTTCT | TCACCATCGC | CGCCTCCAC | CGTGCTCTCG | TTGAGGGTTC | TGCTTTTGCC | 1800 |
| AAGTCCGTCG | GCAGCTCTTG | CAGCGCTTGC | GATGCCATTG | CCCCCCAAAT | TCTGTGCTTC | 1860 |
| CAGCAGAGCT | TCTGGTCCAA | CAGCGGCTAC | ATCATCTCCA | ACTTTGTCAA | CTACCGCAGC | 1920 |
| GGCAAGGACA | TCAACTCCGT | CTTGACTTCC | ATCCACAACT | TCGACCCCGC | TGCCGGTTGC | 1980 |
| GATGTCAACA | CCTTCCAGCC | CTGCAGCGAC | CGGGCTCTTG | CCAACCACAA | GGTTGTCGTT | 2040 |
| GACTCCATGC | GCTTCTGGGG | TGTCAACTCC | GGTCGCACTG | CCGGTAAGGC | CGCCGCTGTC | 2100 |
| GGTCGCTACG | CTGAGGATGT | CTACTACAAC | GGTAACCCGT | GGTACCTCGC | TACTCTCGCC | 2160 |
| GCCGCCGAGC | AGCTCTACGA | CGCCGTCTAC | GTCTGGAAGA | AGCAGGGTTC | TATCACTGTC | 2220 |
| ACCTCCACCT | CCCTCGCCTT | CTTCAAGGAC | CTCGTTCCCT | CCGTCAGCAC | CGGCACCTAC | 2280 |
| TCCAGCTCTT | CCTCCACCTA | CACCGCCATC | ATCAACGCCG | TCACCACCTA | TGCCGACGGC | 2340 |
| TTCGTCGACA | TCGTTGCCCA | GTACACTCCC | TCCGACGGCT | CCCTGGCCGA | GCAGTTCGAC | 2400 |

| | | | | | | |
|---|---|---|---|---|---|---|
| AAGGATTCGG | GCGCCCCCCT | CAGCGCCACC | CACCTGACCT | GGTCGTACGC | CTCCTTCCTT | 2460 |
| TCCGCCGCCG | CCCGCCGCGC | CGGCATCGTC | CCTCCCTCGT | GGGGCGCCGC | GTCCGCCAAC | 2520 |
| TCTCTGCCCG | GTTCCTGCTC | CGCCTCCACC | GTCGCCGGTT | CATACGCCAC | CGCGACTGCC | 2580 |
| ACCTCCTTTC | CCGCCAACCT | CACGCCCGCC | AGCACCACCG | TCACCCCTCC | CACGCAGACC | 2640 |
| GGCTGCGCCG | CCGACCACGA | GGTTTTGGTA | ACTTTCAACG | AAAAGGTCAC | CACCAGCTAT | 2700 |
| GGTCAGACGG | TCAAGGTCGT | CGGCAGCATC | GCTCGGCTCG | GCAACTGGGC | CCCCGCCAGC | 2760 |
| GGGCTCACCC | TGTCGGCCAA | ACAGTACTCT | TCCAGCAACC | CGCTCTGGTC | CACCACTATT | 2820 |
| GCGCTGCCCC | AGGGCACCTC | GTTCAAGTAC | AAGTATGTCG | TCGTCAACTC | GGATGGGTCC | 2880 |
| GTCAAGTGGG | AGAACGATCC | TGACCGCAGC | TATGCTGTTG | GGACGGACTG | CGCCTCTACT | 2940 |
| GCGACTCTTG | ATGATATCCG | GAGGAGGTAA | ATCGCCGGGG | GCGCGCCGGA | TCCTTAATTA | 3000 |
| AGTCTAGAGT | CGACTGTTTA | AACCTGCAGG | CATGCAAGCT | T | | 3041 |

( 2 ) INFORMATION FOR SEQ ID NO: 6:

( i ) SEQUENCE CHARACTERISTICS:
        ( A ) LENGTH: 3718 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Neurospora crassa
        ( B ) STRAIN: Oak Ridge (=St Lawrence) 74A ( v i i ) IMMEDIATE SOURCE:
        ( A ) LIBRARY: lambda J1
        ( B ) CLONE: lambda J1 glam ( x ) PUBLICATION INFORMATION:
        ( A ) AUTHORS: Stone, P J
                Makoff, A J
                Parish, J H
                Radford, A
        ( B ) TITLE: Cloning and sequence analysis of the
                glucoamylase gene of Neurospora crassa
        ( C ) JOURNAL: Curr. Genet.
        ( D ) VOLUME: 24
        ( F ) PAGES: 205-211
        ( G ) DATE: 1993
        ( K ) RELEVANT RESIDUES IN SEQ ID NO: 6: FROM 1 TO 3718

( x i ) SEQUENCE DESCRIPTION: SEQ ID NO: 6:

| | | | | | | |
|---|---|---|---|---|---|---|
| ATCGATGGCA | GCCACCATTC | ATTTCTCGAT | GCGACGGTAA | ACGACGCCCG | CGGCAGATTA | 60 |
| GGTCATTGCC | GAACGGATTG | AAGCTCTCTC | CATCTTGGAT | CCATTCCCGG | CCAATCCCGT | 120 |
| CTCGGCCAAC | CACACTGTCC | ACTCGCCCAG | GTCAGCAGCT | CAGGACTCTC | TCCTGGTTTG | 180 |
| GTACCGCTTA | GTGTAGAGCA | TACCGCTCTC | AGTCCCATA | GACCAACCAT | AACACCGCAC | 240 |
| GTTCTCTTTC | ACTCAAGATG | CTTATCATGT | CCCCTCTTTC | TGCTCCAATG | ATTCGGACTG | 300 |
| GTCGAATACC | AATGAGACAA | GCGAGAGCGC | AGTGCGAGCA | AGCGTTCCTG | CAGATAGAGC | 360 |
| AGTGGGACTG | CCGCGCCACA | AAGGAAGAGG | ATCGTGACGT | GACGTGACCA | GTGACCAGAA | 420 |
| AGCAGAAGAT | CCAAAAGAGT | CAAAAGGACC | GAGCCTCACC | TACAGTAATG | GCCCGGATGG | 480 |
| CACTCAAGAC | CGTCCTCTCG | GCCCTTTCTC | CAACTCTTCT | CCTTCCATAA | TTCACCTAGG | 540 |
| TACATACACG | GCCTACGCTT | CCGCCTCATC | CCATCCCATC | CCATCCCATC | CCATCCCATC | 600 |
| GACGACTCTA | ACCCGCCCGC | GAGTGCAAAC | CTCGTCCACG | AACGGACACC | CCGGCTCTCC | 660 |
| TCCGAAGCCC | TTGCAAGTGG | AAGCTGAGGT | TGCCGAACTT | AGACGACCAG | GTTCACCAGC | 720 |

```
CGGACCGCAA CTCGAACGTC AGAATACAGC CTCAGCCTCC AAAGGGGGTT AACGCCAAGC    780
GAGAGCAAGA CAAGATCGTC GCCCATCAAT ATCCTGGACA AGACAACATG GACGCAATAT    840
ATAACCTCAA GCAAGTCCTC CTCAGCAACC ATGATTTCAC CACCAGCCTG GTCTCCAACG    900
CAACAGACTT CTCGACAAGT CCCTTGACCT ACTTCGCCAT GCATCTCGTC TCTTCGCTCC    960
TCGTCGTGGG CGCCGCCTTC CAGGCCGTGC TCGGTCTGCC GGATCCTCTG CATGAAAAGA   1020
GGCACAGCGA CATCATCAAG CGGTCTGTCG ACTCGTATAT CCAGACCGAG ACTCCCATTG   1080
CGCAGAAGAA CCTTCTGTGC AACATCGGTG CTTCTGGATG CAGAGCCTCC GGTGCTGCCT   1140
CTGGTGTTGT GGTTGCCTCC CCTTCCAAGT CGAGCCCTGA CTGTAAGTGG AAATTGCACA   1200
GTGTGTCTCA TCTCTCATGG CAGCATAGCT CACAGTGTCG ATAGACTGGT ATACCTGGAC   1260
TCGTGATGCC GCCCTTGTCA CCAAGCTTAT TGTCGACGAA TTCACCAACG ACTACAACAC   1320
CACTCTTCAG AACACCATTC AGGCTTATGC TGCTGCACAG GCCAAGCTTC AGGGCGTTAG   1380
CAACCCGTCC GGTTCCCTCT CCAACGGGGC CGGTCTTGGT GAGCCCAAGT TCATGGTCGA   1440
CCTCCAGCAG TTCACCGGTG CCTGGGGCCG CCCCCAGAGG GATGGCCCTC CCCTTCGCGC   1500
CATTGCCCTG ATCGGCTATG GCAAGTGGCT CGTCAGCAAC GGTTATGCTG ATACGGCCAA   1560
GAGCATCATC TGGCCCATTG TGAAGAACGA CCTTGCCTAC ACTGCCAGT ACTGGAACAA    1620
CACTGGCTTC GATCTCTGGG AGGAGGTTAA CAGCTCTTCT TTCTTCACCA TCGCCGCCTC   1680
CCACCGTGCT CTCGTTGAGG GTTCTGCTTT TGCCAAGTCC GTCGGCAGCT CTTGCAGCGC   1740
TTGCGATGCC ATTGCCCCCC AAATTCTGTG CTTCCAGCAG AGCTTCTGGT CCAACAGCGG   1800
CTACATCATC TCCAACTTTG TCAACTACCG CAGCGGCAAG GACATCAACT CCGTCTTGAC   1860
TTCCATCCAC AACTTCGACC CCGCTGCCGG TTGCGATGTC AACACCTTCC AGCCCTGCAG   1920
CGACCGGGCT CTTGCCAACC ACAAGGTTGT CGTTGACTCC ATGCGCTTCT GGGGTGTCAA   1980
CTCCGGTCGC ACTGCCGGTA AGGCCGCCGC TGTCGGTCGC TACGCTGAGG ATGTCTACTA   2040
CAACGGTAAC CCGTGGTACC TCGCTACTCT CGCCGCCGCC GAGCAGCTCT ACGACGCCGT   2100
CTACGTCTGG AAGAAGCAGG GTTCTATCAC TGTCACCTCC ACCTCCCTCG CCTTCTTCAA   2160
GGACCTCGTT CCCTCCGTCA GCACCGGCAC CTACTCCAGC TCTTCCTCCA CCTACACCGC   2220
CATCATCAAC GCCGTCACCA CCTATGCCGA CGGCTTCGTC GACATCGTTG CCCAGTACAC   2280
TCCCTCCGAC GGCTCCCTGG CCGAGCAGTT CGACAAGGAT TCGGGCGCCC CCCTCAGCGC   2340
CACCCACCTG ACCTGGTCGT ACGCCTCCTT CCTTTCCGCC GCCGCCCGCC GCGCCGGCAT   2400
CGTCCCTCCC TCGTGGGGCG CCGCGTCCGC CAACTCTCTG CCCGGTTCCT GCTCCGCCTC   2460
CACCGTCGCC GGTTCATACG CCACCGCGAC TGCCACCTCC TTTCCCGCCA ACCTCACGCC   2520
CGCCAGCACC ACCGTCACCC CTCCCACGCA GACCGGCTGC GCCGCCGACC ACGAGGTTTT   2580
GGTAACTTTC AACGAAAAGG TCACCACCAG CTATGGTCAG ACGGTCAAGG TCGTCGGCAG   2640
CATCGCTCGG CTCGGCAACT GGGCCCCCGC CAGCGGGCTC ACCCTGTCGG CCAAACAGTA   2700
CTCTTCCAGC AACCCGCTCT GGTCCACCAC TATTGCGCTG CCCCAGGGCA CCTCGTTCAA   2760
GTACAAGTAT GTCGTCGTCA ACTCGGATGG GTCCGTCAAG TGGGAGAACG ATCCTGACCG   2820
CAGCTATGCT GTTGGGACGG ACTGCGCCTC TACTGCGACT CTTGATGATA CGTGGAGGTA   2880
AATCGCTTGC TTCGTACTAG GTAGTAAGTA GTGATTGGGA AAAGGAAATG AGAGAACGGG   2940
AACGGGAACG GGAACGGGAA TTTGTGATTA CAAAGTGTAA AATTAATAGG CCCGGGATTT   3000
TGGTTAGATG CATAAGGGGG GCAGGGGGGG CTAGGAAACG GAAGGTTGCA TATCAACCGA   3060
GGAAGAATGG GAAGAAAGGG AAGAAAGACA GAAAGAAGGA ACAACAGGAC TTCATTCTCT   3120
```

-continued

| | | | | | |
|---|---|---|---|---|---|
| CACATCGACA | TGAGCTACCT | GGGCATCAGC | TACCTGGGCA | TCTTGATTTC | CTTTTTAGAA | 3180 |
| GATTGTTTTG | TATCCTTTTT | TCTTCCTCCC | TTTTCTTTTC | TTGTCCGTCT | CTTACACCTA | 3240 |
| CCTATTTTTA | GCCAAAGTCC | ACACACACAC | AAACTTTTTG | TTAGATATTC | TCTGTATCAA | 3300 |
| AATTGACAAG | TTTCAATGTT | ATACAGTACC | TTGCCAAGTT | TAATACACAT | TCAAATCAAT | 3360 |
| CAACCACACA | CACACAAGTT | TTATTGTGCA | GAAATGGAGT | GAAGAAGAAA | CATGTTTGGG | 3420 |
| ATTATGATGA | CAAGCTTCTC | AACAAAATTT | CAACGAGTTA | AGCTTCAAAG | GTCCGCTGGC | 3480 |
| TCAATGGCAG | AGCGTCTGAC | TACGAATCAG | GAGGTTCCAG | GTTCGACCCC | TGGGTGGATC | 3540 |
| GAGTTGCAAA | TTGGTACTTT | GAGTACCAAA | GTTCCTTTTT | TTTTTTCGTT | TGGCTCTCTG | 3600 |
| CTTTTCGACA | GTTCACTGAG | TCATGTGCAA | GACACCCTG | ATCGGGTACG | TACTGAACTG | 3660 |
| CTTTTGGTGC | AGTGCAATGG | TTCTCGAGTG | CAAGGGATGA | AAGGAAGATA | TGTCTTGG | 3718 |

( 2 ) INFORMATION FOR SEQ ID NO:7:

( i ) SEQUENCE CHARACTERISTICS:
        ( A ) LENGTH: 626 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE:

( x i ) SEQUENCE DESCRIPTION: SEQ ID NO:7:

```
Met His Leu Val Ser Ser Leu Leu Val Val Gly Ala Ala Phe Gln Ala
 1               5                  10                  15

Val Leu Gly Leu Pro Asp Pro Leu His Glu Lys Arg His Ser Asp Ile
                20                  25                  30

Ile Lys Arg Ser Val Asp Ser Tyr Ile Gln Thr Glu Thr Pro Ile Ala
            35                  40                  45

Gln Lys Asn Leu Leu Cys Asn Ile Gly Ala Ser Gly Cys Arg Ala Ser
        50                  55                  60

Gly Ala Ala Ser Gly Val Val Ala Ser Pro Ser Lys Ser Ser Pro
 65                  70                  75                  80

Asp Tyr Trp Tyr Thr Trp Thr Arg Asp Ala Ala Leu Val Thr Lys Leu
                85                  90                  95

Ile Val Asp Glu Phe Thr Asn Asp Tyr Asn Thr Thr Leu Gln Asn Thr
               100                 105                 110

Ile Gln Ala Tyr Ala Ala Ala Gln Ala Lys Leu Gln Gly Val Ser Asn
           115                 120                 125

Pro Ser Gly Ser Leu Ser Asn Gly Ala Gly Leu Gly Glu Pro Lys Phe
       130                 135                 140

Met Val Asp Leu Gln Gln Phe Thr Gly Ala Trp Gly Arg Pro Gln Arg
145                 150                 155                 160

Asp Gly Pro Pro Leu Arg Ala Ile Ala Leu Ile Gly Tyr Gly Lys Trp
                165                 170                 175

Leu Val Ser Asn Gly Tyr Ala Asp Thr Ala Lys Ser Ile Ile Trp Pro
               180                 185                 190

Ile Val Lys Asn Asp Leu Ala Tyr Thr Ala Gln Tyr Trp Asn Asn Thr
           195                 200                 205

Gly Phe Asp Leu Trp Glu Glu Val Asn Ser Ser Ser Phe Phe Thr Ile
       210                 215                 220
```

```
Ala  Ala  Ser  His  Arg  Ala  Leu  Val  Glu  Gly  Ser  Ala  Phe  Ala  Lys  Ser
225                      230                      235                      240

Val  Gly  Ser  Ser  Cys  Ser  Ala  Cys  Asp  Ala  Ile  Ala  Pro  Gln  Ile  Leu
                    245                      250                     255

Cys  Phe  Gln  Gln  Ser  Phe  Trp  Ser  Asn  Ser  Gly  Tyr  Ile  Ile  Ser  Asn
               260                      265                     270

Phe  Val  Asn  Tyr  Arg  Ser  Gly  Lys  Asp  Ile  Asn  Ser  Val  Leu  Thr  Ser
          275                      280                     285

Ile  His  Asn  Phe  Asp  Pro  Ala  Ala  Gly  Cys  Asp  Val  Asn  Thr  Phe  Gln
     290                     295                      300

Pro  Cys  Ser  Asp  Arg  Ala  Leu  Ala  Asn  His  Lys  Val  Val  Asp  Ser
305                      310                      315                      320

Met  Arg  Phe  Trp  Gly  Val  Asn  Ser  Gly  Arg  Thr  Ala  Gly  Lys  Ala  Ala
                    325                      330                     335

Ala  Val  Gly  Arg  Tyr  Ala  Glu  Asp  Val  Tyr  Tyr  Asn  Gly  Asn  Pro  Trp
               340                      345                     350

Tyr  Leu  Ala  Thr  Leu  Ala  Ala  Ala  Glu  Gln  Leu  Tyr  Asp  Ala  Val  Tyr
          355                      360                     365

Val  Trp  Lys  Lys  Gln  Gly  Ser  Ile  Thr  Val  Thr  Ser  Thr  Ser  Leu  Ala
     370                      375                      380

Phe  Phe  Lys  Asp  Leu  Val  Pro  Ser  Val  Ser  Thr  Gly  Thr  Tyr  Ser  Ser
385                      390                      395                      400

Ser  Ser  Ser  Thr  Tyr  Thr  Ala  Ile  Ile  Asn  Ala  Val  Thr  Thr  Tyr  Ala
                    405                      410                     415

Asp  Gly  Phe  Val  Asp  Ile  Val  Ala  Gln  Tyr  Thr  Pro  Ser  Asp  Gly  Ser
               420                      425                     430

Leu  Ala  Glu  Gln  Phe  Asp  Lys  Asp  Ser  Gly  Ala  Pro  Leu  Ser  Ala  Thr
          435                      440                     445

His  Leu  Thr  Trp  Ser  Tyr  Ala  Ser  Phe  Leu  Ser  Ala  Ala  Ala  Arg  Arg
     450                      455                      460

Ala  Gly  Ile  Val  Pro  Pro  Ser  Trp  Gly  Ala  Ala  Ser  Ala  Asn  Ser  Leu
465                      470                      475                      480

Pro  Gly  Ser  Cys  Ser  Ala  Ser  Thr  Val  Ala  Gly  Ser  Tyr  Ala  Thr  Ala
                    485                      490                     495

Thr  Ala  Thr  Ser  Phe  Pro  Ala  Asn  Leu  Thr  Pro  Ala  Ser  Thr  Thr  Val
               500                      505                     510

Thr  Pro  Pro  Thr  Gln  Thr  Gly  Cys  Ala  Ala  Asp  His  Glu  Val  Leu  Val
          515                      520                     525

Thr  Phe  Asn  Glu  Lys  Val  Thr  Thr  Ser  Tyr  Gly  Gln  Thr  Val  Lys  Val
     530                      535                      540

Val  Gly  Ser  Ile  Ala  Arg  Leu  Gly  Asn  Trp  Ala  Pro  Ala  Ser  Gly  Leu
545                      550                      555                      560

Thr  Leu  Ser  Ala  Lys  Gln  Tyr  Ser  Ser  Ser  Asn  Pro  Leu  Trp  Ser  Thr
                    565                      570                     575

Thr  Ile  Ala  Leu  Pro  Gln  Gly  Thr  Ser  Phe  Lys  Tyr  Lys  Tyr  Val  Val
               580                      585                     590

Val  Asn  Ser  Asp  Gly  Ser  Val  Lys  Trp  Glu  Asn  Asp  Pro  Asp  Arg  Ser
          595                      600                     605

Tyr  Ala  Val  Gly  Thr  Asp  Cys  Ala  Ser  Thr  Ala  Thr  Leu  Asp  Asp  Thr
     610                      615                      620

Trp  Arg
625
```

( 2 ) INFORMATION FOR SEQ ID NO:8:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "5'primer at the Ppum I site"

( i i i ) HYPOTHETICAL: NO ( x i ) SEQUENCE DESCRIPTION: SEQ ID NO:8:

CCTTCTTCAA GGACCTCGTT CCCTCCG 27

( 2 ) INFORMATION FOR SEQ ID NO:9:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "5'primer"

( i i i ) HYPOTHETICAL: NO ( x i ) SEQUENCE DESCRIPTION: SEQ ID NO:9:

CCTTCTTCAA GGACCTCGTT CCCTCCG 27

( 2 ) INFORMATION FOR SEQ ID NO:10:

( i ) SEQUENCE CHARACTERISTICS:
    ( A ) LENGTH: 46 base pairs
    ( B ) TYPE: nucleic acid
    ( C ) STRANDEDNESS: double
    ( D ) TOPOLOGY: linear ( i i ) MOLECULE TYPE: other nucleic acid
    ( A ) DESCRIPTION: /desc = "fragment of glucoamylase gene"

( i i i ) HYPOTHETICAL: NO ( x i ) SEQUENCE DESCRIPTION: SEQ ID NO:10:

CCACCTCCCT CGCCTTCTTC AAGGACCTCG TTCCCTCCGT CAGCAC 46

( 2 ) INFORMATION FOR SEQ ID NO:11:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "3'primer at the Mro I site"

( i i i ) HYPOTHETICAL: NO ( x i ) SEQUENCE DESCRIPTION: SEQ ID NO:11:

GCTGAGAACT ACTATAGGCC TCCATTTAGC GG 32

( 2 ) INFORMATION FOR SEQ ID NO:12:

( i ) SEQUENCE CHARACTERISTICS:
    ( A ) LENGTH: 49 base pairs
    ( B ) TYPE: nucleic acid
    ( C ) STRANDEDNESS: double (D) TOPOLOGY: linear (ii) MOLECULE TYPE: other nucleic acid
    (A) DESCRIPTION: /desc = "fragment of glucoamylase gene"

(iii) HYPOTHETICAL: NO (xi) SEQUENCE DESCRIPTION: SEQ ID NO:12:

TACTGCGACT CTTGATGATA CGTGGAGGTA AATCGCTTGC TTCGTACTA  49

(2) INFORMATION FOR SEQ ID NO:13:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "3'primer"

(iii) HYPOTHETICAL: NO (xi) SEQUENCE DESCRIPTION: SEQ ID NO:13:

CGCTAAATGG AGGCCTATAG TAGTTCTCAG CG  32

(2) INFORMATION FOR SEQ ID NO:14:

(i) SEQUENCE CHARACTERISTICS:
    (A) LENGTH: 626 amino acids
    (B) TYPE: amino acid
    (C) STRANDEDNESS: single
    (D) TOPOLOGY: linear (ii) MOLECULE TYPE: protein (iii) HYPOTHETICAL: NO (v) FRAGMENT TYPE:

(xi) SEQUENCE DESCRIPTION: SEQ ID NO:14:

| Met | His | Leu | Val | Ser | Ser | Leu | Leu | Val | Val | Gly | Ala | Ala | Phe | Gln | Ala |
| 1 | | | | 5 | | | | | 10 | | | | | 15 | |

| Val | Leu | Gly | Leu | Pro | Asp | Pro | Leu | His | Glu | Lys | Arg | His | Ser | Asp | Ile |
| | | | 20 | | | | | 25 | | | | | 30 | | |

| Ile | Lys | Arg | Ser | Val | Asp | Ser | Tyr | Ile | Gln | Thr | Glu | Thr | Pro | Ile | Ala |
| | | 35 | | | | | 40 | | | | | 45 | | | |

| Gln | Lys | Asn | Leu | Leu | Cys | Asn | Ile | Gly | Ala | Ser | Gly | Cys | Arg | Ala | Ser |
| | 50 | | | | | 55 | | | | | 60 | | | | |

| Gly | Ala | Ala | Ser | Gly | Val | Val | Val | Ala | Ser | Pro | Ser | Lys | Ser | Ser | Pro |
| 65 | | | | | 70 | | | | | 75 | | | | | 80 |

| Asp | Tyr | Trp | Tyr | Thr | Trp | Thr | Arg | Asp | Ala | Ala | Leu | Val | Thr | Lys | Leu |
| | | | | 85 | | | | | 90 | | | | | 95 | |

| Ile | Val | Asp | Glu | Phe | Thr | Asn | Asp | Tyr | Asn | Thr | Thr | Leu | Gln | Asn | Thr |
| | | | | 100 | | | | | 105 | | | | | 110 | |

| Ile | Gln | Ala | Tyr | Ala | Ala | Ala | Gln | Ala | Lys | Leu | Gln | Gly | Val | Ser | Asn |
| | | | 115 | | | | | 120 | | | | | 125 | | |

| Pro | Ser | Gly | Ser | Leu | Ser | Asn | Gly | Ala | Gly | Leu | Gly | Glu | Pro | Lys | Phe |
| | | 130 | | | | | 135 | | | | | 140 | | | |

| Met | Val | Asp | Leu | Gln | Gln | Phe | Thr | Gly | Ala | Trp | Gly | Arg | Pro | Gln | Arg |
| 145 | | | | | 150 | | | | | 155 | | | | | 160 |

| Asp | Gly | Pro | Pro | Leu | Arg | Ala | Ile | Ala | Leu | Ile | Gly | Tyr | Gly | Lys | Trp |
| | | | | 165 | | | | | 170 | | | | | 175 | |

```
Leu  Val  Ser  Asn  Gly  Tyr  Ala  Asp  Thr  Ala  Lys  Ser  Ile  Ile  Trp  Pro
               180                 185                      190

Ile  Val  Lys  Asn  Asp  Leu  Ala  Tyr  Thr  Ala  Gln  Tyr  Trp  Asn  Asn  Thr
          195                      200                 205

Gly  Phe  Asp  Leu  Trp  Glu  Glu  Val  Asn  Ser  Ser  Phe  Phe  Thr  Ile
     210                      215                 220

Ala  Ala  Ser  His  Arg  Ala  Leu  Val  Glu  Gly  Ser  Ala  Phe  Ala  Lys  Ser
225                           230                 235                      240

Val  Gly  Ser  Ser  Cys  Ser  Ala  Cys  Asp  Ala  Ile  Ala  Pro  Gln  Ile  Leu
               245                 250                           255

Cys  Phe  Gln  Gln  Ser  Phe  Trp  Ser  Asn  Ser  Gly  Tyr  Ile  Ile  Ser  Asn
               260                 265                      270

Phe  Val  Asn  Tyr  Arg  Ser  Gly  Lys  Asp  Ile  Asn  Ser  Val  Leu  Thr  Ser
          275                      280                 285

Ile  His  Asn  Phe  Asp  Pro  Ala  Ala  Gly  Cys  Asp  Val  Asn  Thr  Phe  Gln
     290                      295                 300

Pro  Cys  Ser  Asp  Arg  Ala  Leu  Ala  Asn  His  Lys  Val  Val  Val  Asp  Ser
305                           310                 315                      320

Met  Arg  Phe  Trp  Gly  Val  Asn  Ser  Gly  Arg  Thr  Ala  Gly  Lys  Ala  Ala
               325                      330                      335

Ala  Val  Gly  Arg  Tyr  Ala  Glu  Asp  Val  Tyr  Tyr  Asn  Gly  Asn  Pro  Trp
               340                      345                 350

Tyr  Leu  Ala  Thr  Leu  Ala  Ala  Ala  Glu  Gln  Leu  Tyr  Asp  Ala  Val  Tyr
               355                 360                 365

Val  Trp  Lys  Lys  Gln  Gly  Ser  Ile  Thr  Val  Thr  Ser  Thr  Ser  Leu  Ala
     370                      375                 380

Phe  Phe  Lys  Asp  Leu  Val  Pro  Ser  Val  Ser  Thr  Gly  Thr  Tyr  Ser  Ser
385                      390                 395                           400

Ser  Ser  Ser  Thr  Tyr  Thr  Ala  Ile  Ile  Asn  Ala  Val  Thr  Thr  Tyr  Ala
               405                      410                      415

Asp  Gly  Phe  Val  Asp  Ile  Val  Ala  Gln  Tyr  Thr  Pro  Ser  Asp  Gly  Ser
               420                 425                      430

Leu  Ala  Glu  Gln  Phe  Asp  Lys  Asp  Ser  Gly  Ala  Pro  Leu  Ser  Ala  Thr
               435                 440                      445

His  Leu  Thr  Trp  Ser  Tyr  Ala  Ser  Phe  Leu  Ser  Ala  Ala  Ala  Arg  Arg
               450                 455                      460

Ala  Gly  Ile  Val  Pro  Pro  Ser  Trp  Gly  Ala  Ala  Ser  Ala  Asn  Ser  Leu
465                      470                      475                      480

Pro  Gly  Ser  Cys  Ser  Ala  Ser  Thr  Val  Ala  Gly  Ser  Tyr  Ala  Thr  Ala
               485                      490                      495

Thr  Ala  Thr  Ser  Phe  Pro  Ala  Asn  Leu  Thr  Pro  Ala  Ser  Thr  Thr  Val
               500                 505                      510

Thr  Pro  Pro  Thr  Gln  Thr  Gly  Cys  Ala  Ala  Asp  His  Glu  Val  Leu  Val
               515                 520                      525

Thr  Phe  Asn  Glu  Lys  Val  Thr  Thr  Ser  Tyr  Gly  Gln  Thr  Val  Lys  Val
          530                      535                 540

Val  Gly  Ser  Ile  Ala  Arg  Leu  Gly  Asn  Trp  Ala  Pro  Ala  Ser  Gly  Leu
545                      550                      555                      560

Thr  Leu  Ser  Ala  Lys  Gln  Tyr  Ser  Ser  Asn  Pro  Leu  Trp  Ser  Thr
               565                      570                      575

Thr  Ile  Ala  Leu  Pro  Gln  Gly  Thr  Ser  Phe  Lys  Tyr  Lys  Tyr  Val  Val
               580                      585                 590

Val  Asn  Ser  Asp  Gly  Ser  Val  Lys  Trp  Glu  Asn  Asp  Pro  Asp  Arg  Ser
          595                      600                 605
```

```
Tyr Ala Val Gly Thr Asp Cys Ala Ser Thr Ala Thr Leu Asp Asp Thr
    610                 615                 620
Trp Arg
625
```

We claim:

1. A construct including at least the regulated promoter sequence of the gene encoding the protein glucoamylase of *Neurospora crassa* and further including at least one restriction site whereby a coding sequence for a heterologous peptide can be introduced into the gene so a heterologous peptide is expressed under the control of said promoter sequence.

2. A construct according to claim 1 wherein the promoter sequence includes an upstream activator comprising the TATA box at position -101 with respect to the start codon ATG shown in FIG. 1 (SEQ ID NO 6).

3. A construct according to claim 1 comprising plasmid pPS8.

4. A construct according to claim 1 comprising the plasmid pGla-Xho I.

5. A construct according to claim 1 comprising the plasmid pGla-Mro I.

6. A construct according to claim 1 comprising the plasmid pGE.

7. A construct according to claim 1 comprising the plasmid pGla XL.

8. A construct according to claim 1 comprising the plasmid pGla XLX.

9. A construct according to claim 1 comprising the plasmid pGLa MXLX.

10. A construct according to claim 1 comprising the plasmid pGS.

11. The regulated promoter of claim 1 which has the DNA sequence structure shown in FIG. 1 (SEQ ID NO:6).

12. A construct according to claim 1, wherein the promoter sequence includes an upstream activator comprising the CAAT box at position -133 with respect to the start codon ATG shown in FIG. 1 (SEQ ID NO. 6).

13. A construct according to claim 12 wherein the promoter sequence comprises the first 938 nucleotides of the DNA sequence structure shown in FIG. 1 (SEQ ID NO: 6).

14. A construct according to claim 1 wherein the construct further includes a Neurospora-selectable marker.

15. A construct according to claim 14 wherein said marker provides hygromycin-resistance.

16. A construct according to claim 15 wherein said construct further comprises an *E. coli*-selectable marker.

17. A construct according to claim 16 wherein said marker is a gene encoding ampicillin-resistance.

18. A construct according to claim 1 wherein the construct further comprises DNA sequence structure encoding a secretion signal sequence.

19. A construct according to claim 18 wherein said DNA sequence structure is translationally fused to the codon sequence of a heterologous peptide.

20. A method for transforming filamentous fungus comprising:

(a) introducing the DNA construct of claim 1, linked to a selectable marker, into a filamentous fungal cell; and (b) culturing said filamentous fungal cell in the presence of an agent to which said selectable marker confers resistance; and (c) monitoring resistant colonies of said filamentous fungal cells for the production of a heterologous polypeptide;

(d) wherein said filamentous fungal cells are transformed.

21. A method according to claim 20 herein said filamentous fungus is *Neurospora crassa*.

22. A method for the production of a pre-selected heterologous peptide from at least one filamentous fungus comprising:

a) providing a construct in accordance with claim 20 modified to include a gene encoding a heterologous peptide, b) transforming a pre-selected species of filamentous fungus with said construct, c) culturing said transformed fungus; and d) harvesting the heterologous peptide provided in said construct.

23. A method according to claim 22 wherein said filamentous fungus is *Neurospora crassa*.

24. A filamentous fungi having inserted therein a construct in accordance with claim 1.

25. A filamentous fungi according to claim 24 wherein said fungi is *Neurospora crassa*.

26. A primer comprising at least one of the sequence structures shown in FIG. 4, SEQ ID NO:8, SEQ ID NO:9, SEQ ID NO:10, SEQ ID NO:11, SEQ ID NO:12 or SEQ ID NO:13.

* * * * *